(12) United States Patent
Blumenfeld et al.

(10) Patent No.: US 9,580,451 B2
(45) Date of Patent: Feb. 28, 2017

(54) SULFONIC ESTERS OF METAL OXIDES AND METHODS OF THEIR USE

(71) Applicants: California Institute of Technology, Pasadena, CA (US); Children's Hospital of Los Angeles, Los Angeles, CA (US)

(72) Inventors: Carl M. Blumenfeld, Pasadena, CA (US); Harry B. Gray, Pasadena, CA (US); Robert H. Grubbs, South Pasadena, CA (US); Karn Sorasaenee, Altadena, CA (US)

(73) Assignees: California Institute of Technology, Pasadena, CA (US); Children's Hospital of Los Angeles, Los Angeles, CA (US)

( * ) Notice: Subject to any disclaimer, the term of this patent is extended or adjusted under 35 U.S.C. 154(b) by 0 days.

(21) Appl. No.: 14/604,917

(22) Filed: Jan. 26, 2015

(65) Prior Publication Data
US 2015/0141640 A1    May 21, 2015

Related U.S. Application Data

(62) Division of application No. 14/178,592, filed on Feb. 12, 2014, now Pat. No. 8,968,789.

(60) Provisional application No. 61/764,127, filed on Feb. 13, 2013.

(51) Int. Cl.
| | |
|---|---|
| *C07F 7/28* | (2006.01) |
| *C07D 487/22* | (2006.01) |
| *C07F 5/00* | (2006.01) |
| *C07F 5/06* | (2006.01) |
| *A61K 49/00* | (2006.01) |

(52) U.S. Cl.
CPC .............. *C07F 7/28* (2013.01); *C07D 487/22* (2013.01); *C07F 5/003* (2013.01); *C07F 5/069* (2013.01); *A61K 49/0021* (2013.01); *A61K 49/0065* (2013.01); *A61K 49/0067* (2013.01); *B01J 2531/025* (2013.01)

(58) Field of Classification Search
CPC ............ A61K 49/0021; A61K 49/0065; A61K 49/0067; C07F 7/28; C07F 5/003; C07F 5/0064; C07D 487/22; B01J 2531/025
See application file for complete search history.

(56) References Cited

U.S. PATENT DOCUMENTS 2,683,143 A * 7/1954 White ................ C08B 3/14
                                                536/31
2006/0281087 A1* 12/2006 Sonezaki ............ A61K 9/0014
                                                435/6.11

| | | |
|---|---|---|
| 2010/0305335 A1 | 12/2010 | Palmer et al. |
| 2011/0098262 A1 | 4/2011 | Yondim et al. |
| 2011/0144078 A1 | 6/2011 | Gross et al. |

FOREIGN PATENT DOCUMENTS

WO       WO 00/75144 A2    12/2000

OTHER PUBLICATIONS

Andersson et al., Consecutive microcontact printing-ligands for asymmetric catalysis in silicon channels, 2001, Sensors and Actuators B, vol. 79, pp. 78-84.*
Nelles et al., Functionalization of silicon nanoparticles via hydrosilylation with 1-alkenes, Jan. 20, 2007, Colloid Polym. Sci. vol. 285, pp. 729-736.*
Nilssonet al., Immobilization of Ligands with Organic Sulfonyl Chloride, 1984, Methods of Enzymology, vol. 104, p. 56-69.*
Accardo, et al., "Peptide-based Targeting Strategies for Simultaneous Imaging and Therapy with Nanovectors" Polymer J., May 2013, 45, 481-93.
Agadjanian et al, "Specific Delivery of Corroles to Cells via Noncovalent Conjugates with Viral Proteins", Pharmaceutical Research, Feb. 2006, 23(2), 367-377.
Aina, et al., "Therapeutic Cancer Targeting Peptides", Biopolymers, Oct. 2002, 66(3), 184-99.
Allen, "Ligand-Targeted Therapeutics in Anticancer Therapy", Nature Rev. Cancer, Oct. 2, 2002, 2(10), 750-63.
Almadhoun et al, "Nanocomposites of Ferroelectric Polymers With Surface-Hydroxylated BaTiO3 Nanoparticles for Energy Storage Applications", Chem., May 2012, 22, 11196.
Arkles, "Silane Coupling Agents Connecting Across Boundaries", 2006, Version 2.0, 60 pages.

(Continued)

*Primary Examiner* — Ali Soroush
(74) *Attorney, Agent, or Firm* — Baker & Hostetler LLP

(57) ABSTRACT

The present invention is directed to sulfonic esters of metal oxides including those of formulas I and II:

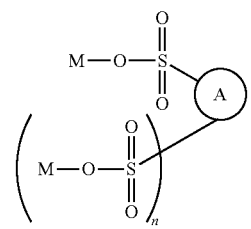

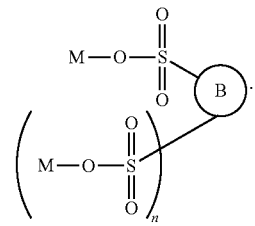

8 Claims, 10 Drawing Sheets

(56) References Cited

OTHER PUBLICATIONS

Autret et al, "Synthesis and Electrochemistry of Iron( 111) Corroles Containing a Nitrosyl Axial Ligand. Spectral Characterization of [(OEC)FeTII(NO)]nW here n=0, 1, 2, or -1 and OEC is the Trianion of 2,3,7,8,12,13,17,18-Octaethylcorrol", J. Am. Chem. Soc., 1994,116, 9141-9149.
Aviv et al, "Corrole-Based Applications", Chemical Communications, May 28, 2007, 1987-1999.
Barata et al., "Corrole-Silica Hybrid Particles: Synthesis and Effects on Singlet Oxygen Generation", RSC Adv., Oct. 24, 2012, 3, 274-80.
Barbe et al, "Metallocorroles as Sensing Components for Gas Sensors: Remarkable Affinity and Selectivity of Cobalt(III) Corroles for Co vs. O2 and N2", The Royal Society of Chemistry, Mar. 23, 2004, 1208-1214.
Blumenfeld et al, "Decorating Metal Oxide Surfaces with Fluorescent Chlorosulfonated Corroles", Inorganic Chemistry, Apr. 2013, 52, 4774-4776.
Haber et al, "Protecting the Beneficial Functionality of Lipoproteins by 1-fe, A Corrole-Based Catalytic Antioxidant", Chem. Sci., 2011, 2, 295-302.
Hori, T. and Osuka, A., "Nucleophilic Substitution Reactions of meso-5,10,15-Tris(pentafluorophenyl)-corrole; Synthesis of ABC-Type Corroles and Corrole-Based Organogels", Eur. J. Org. Chem., 2010, 2379-2386.
Hwang et al, "Photoexcitation of Tumor-Targeted Corroles Induces Singlet Oxygen-Mediated Augmentation of Cytotoxicity", Journal of Controlled Release, 2012, 163, 368-373.
Ikeda, et al., "Lateral Distribution of N3 Dye Molecules on TiO2 (110) Surface", Journal of Photochemistry, 2009, 202, pp. 185-190.
Jaracz, et al., "Recent Advances in Tumor-Targeting Anticancer Drug Conjugates" Bioorg. Med. Chem., Dec. 2005, 13(17), 5043-54.
Jin, et al., "Targeted Delivery System of Nanobiomaterials in Anticancer Therapy from Cells to Clinics", BioMed. Res. Inti., Feb. 2014, 24 pages.

Kanamoril et al, "Neuroprotection Against Superoxide Anion Radical by Metallocorroles in Cellular and Murine Models of Optic Neuropathy", Journal of Neurochemistry, 2010, 114, 488-498.
Mahammed et al, "Highly Selective Chlorosulfonation of Tris(Pentafluorophenyl)Corrole as a Synthetic Tool for the Preparation of Amphiphilic Corroles and Metal Complexes of Planar Chirality", Organic Letters, Nov. 1, 2001, 3(22), 3443-3436.
Palmer, J., "Transition Metal Corrole Coordination Chemistry", Struct Bond, 2012, 142: 49-90, Published online: Sep. 14, 2011.
Saltsman et al, "Selective Substitution of Corroles: Nitration, Hydroformylation, and Chlorosulfonation", J. Am. Chem. Soc. Jun. 26, 2002, 124(25):7411-20.
Sapsford, et al., "Functionalizing Nanoparticles with Biological Molecules:Developing Chemistires that Facilitate Nanotechnology", American Chemical Society, Feb. 22, 2013, pp. 1904-2074.
Simkhovich et al, "Mono- and Binuclear Ruthenium Corroles: Synthesis, Spectroscopy, Electrochemistry, and Structural Characterization", Chem. Eur. J. 2003, 9(1), 201-208.
Simkhovich et al, "Synthesis and Characterization of Germanium, Tin, Phosphorus, Iron, and Rhodium Complexes of Tris(pentafluorophenyl)corrole, and the Utilization of the Iron and Rhodium Corroles as Cyclopropanation Catalysts", Chem. Eur. J., 2001, 7(5), 1041-1055.
Tamura, et al., "Mechanism of Hydroxylation of Metal Oxide Surfaces", Journal of Colloid and Interface Sci., Nov. 2001, 243(1), 202-207.
Tortora et al, "Supramolecular Sensing Mechanism of Corrole Thin Films", Sensor and Actuartors B, 2013, 187, 72-77.
Viskota, et al., "Surface Functionalization of Barium Titanate SHG Nanoprobes for In Vivo Imaging in Zebrafish", Protocol, vol. 7(9), Aug. 9, 2012, pp. 1618-1633.
Wang, et al., "Characteristics of High Efficiency Dye-Sensitized Solar Cells." Journal of Physical Chemistry B, vol. 110, 2006, pp. 25210-25221.
Weaver. "Corrales." PhD Thesis—California Institute of Technology, May 5, 2005. pp. i-xvi and 1-116.

\* cited by examiner (a) (b) (c)

SULFONIC ESTERS OF METAL OXIDES AND METHODS OF THEIR USE

CROSS REFERENCE TO RELATED APPLICATIONS

This application is a divisional of U.S. Ser. No. 14/178,592, filed Feb. 12, 2014, which claims the benefit of U.S. Provisional Application No. 61/764,127, filed Feb. 13, 2013, the entireties of which are incorporated by reference herein.

TECHNICAL FIELD

The present invention is directed to sulfonic esters of metal oxides and their uses.

BACKGROUND

Corroles are tetrapyrrolic macrocycles:

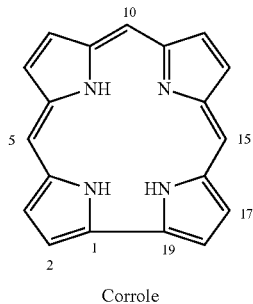 [SMILES: C1=Cc2cc3ccc([nH]3)c3ccc(cc4ccc(cc1n2)[nH]4)[nH]3]

Corrole

Corroles are becoming increasing useful in the field of chemical synthesis as catalysts in, for example, oxidation, hydroxylation, hydroperoxidation, epoxidation, sulfoxidation, reduction, and group transfer reactions. See, e.g., Aviv, I., Gross, Z., *Chem. Commun.*, 2007, 1987-1999. Based on their physico-chemical properties, it is envisioned that corroles could be useful in the sensors field and biomedical field. Id. Corrole-based materials useful in the chemical synthesis, sensor, biomedical, and other fields are needed.

SUMMARY

The present invention is directed to materials of formula I:

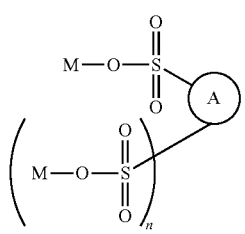

wherein A is a corrolyl or metallated corrolyl; M is a surface comprising $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SnO_2$, $SiO_2$, or $ZnO$; and n is 0 or 1.

The invention is also directed to materials according to formula II:

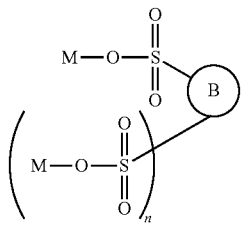

wherein B is —NCO, $C_{1-10}$alkyl, or

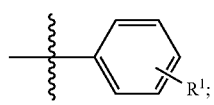

wherein $R^1$ is —COOH, —COO$C_{1-6}$alkyl, $C_{1-6}$alkyl, or aryl optionally substituted with halogen or $C_{1-6}$alkyl; M is a surface comprising $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SnO_2$, $SiO_2$, or $ZnO$; and n is 0 or 1.

Methods of making materials of formulas I and II are described herein. Also described are methods of using the materials of the invention in applications such as optical imaging.

DETAILED DESCRIPTION OF ILLUSTRATIVE EMBODIMENTS

Figure 1:
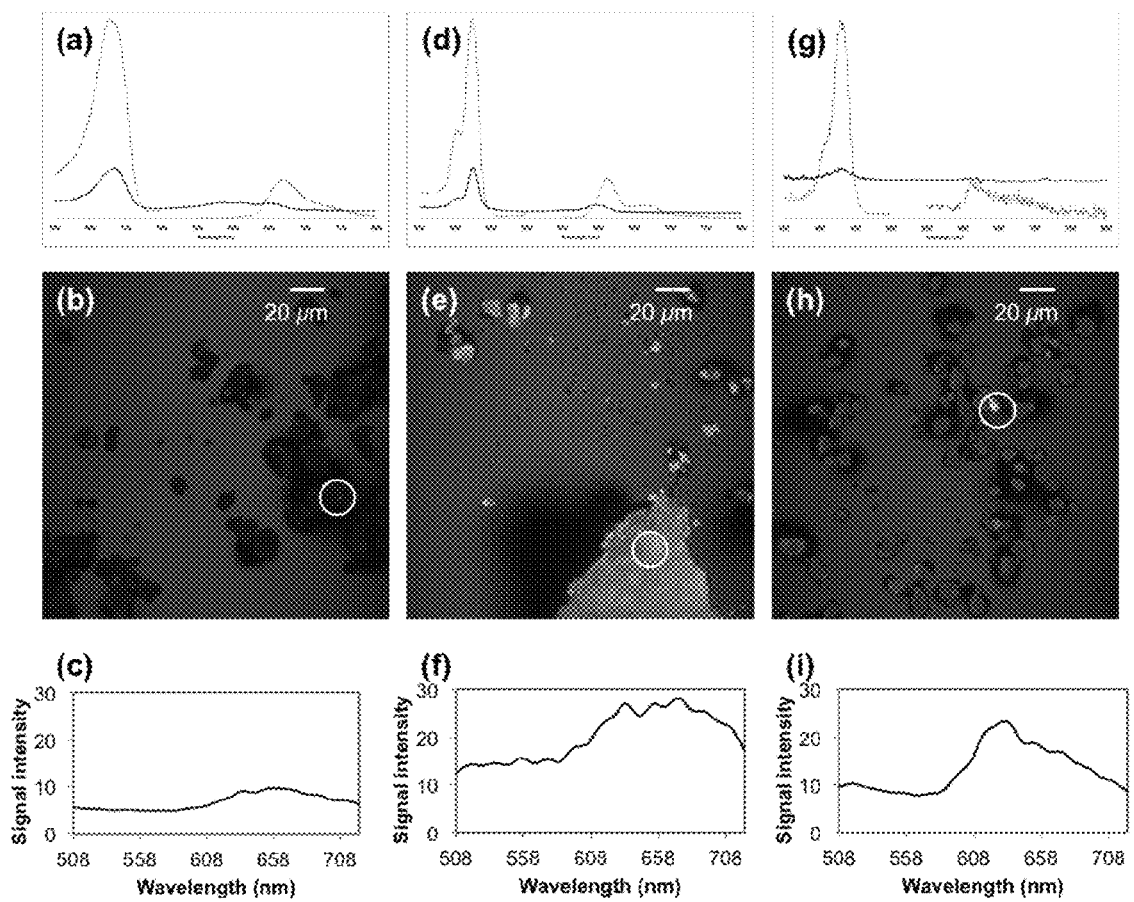
FIG. 1 depicts confocal fluorescence microscopy images of 1-$TiO_2$ [(a), (b), (c)], 1-Al—$TiO_2$ [(d), (e), (0], and 1-Ga—$TiO_2$ [(d), (e), (f)].

The present invention is directed to materials, preferably nanoparticulate materials, comprising a metal oxide covalently bonded to a corrole or metallated-corrole through an —SO$_2$— linkage. The metal oxides for use in making the materials of the invention include those having at least one —OH group. Such metal oxides are known in the art and are described in further detail below.

One embodiment of the invention is directed to materials according to formula I:

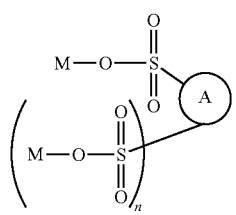

I wherein A is a corrolyl or metallated corrolyl;
M is a surface comprising TiO$_2$, BaTiO$_3$, SnO$_2$, Al$_2$O$_3$, Fe$_2$O$_3$, Fe$_3$O$_4$, ZrO$_2$, CeO$_2$, CdO, Cr$_2$O$_3$, CuO, MnO, Mn$_2$O$_3$, MnO$_2$, NiO, SnO, SnO$_2$, SiO$_2$, or ZnO; and
n is 0 or 1.

Within the scope of the invention, M is a surface that comprises a metal oxide, for example, a metal oxide that comprises at least one —OH group. The —OH group can be inherently present on the surface. Alternatively, the at least one —OH group can be incorporated by oxidizing the surface with a reagent such as hydrogen peroxide. Preferred surfaces for use in the invention include metal oxides such as TiO$_2$, BaTiO$_3$, SnO$_2$, Al$_2$O$_3$, Fe$_2$O$_3$, Fe$_3$O$_4$, ZrO$_2$, CeO$_2$, CdO, Cr$_2$O$_3$, CuO, MnO, Mn$_2$O$_3$, MnO$_2$, NiO, SnO, SnO$_2$, SiO$_2$, and ZnO. In some embodiments, the surface comprises TiO$_2$. In some embodiments, the surface comprises BaTiO$_3$. In some embodiments, the surface comprises SnO$_2$. In some embodiments, the surface comprises Al$_2$O$_3$. In some embodiments, the surface comprises Fe$_2$O$_3$. In some embodiments, the surface comprises Fe$_3$O$_4$. In some embodiments, the surface comprises ZrO$_2$. In some embodiments, the surface comprises CeO$_2$. In some embodiments, the surface comprises CdO. In some embodiments, the surface comprises Cr$_2$O$_3$. In some embodiments, the surface comprises CuO. In some embodiments, the surface comprises MnO. In some embodiments, the surface comprises Mn$_2$O$_3$. In some embodiments, the surface comprises MnO$_2$. In some embodiments, the surface comprises NiO. In some embodiments, the surface comprises SnO. In some embodiments, the surface comprises SnO$_2$. In some embodiments, the surface comprises SiO$_2$. In some embodiments, the surface comprises ZnO.

In preferred embodiments, the surface is a nanoparticle surface.

In some embodiments, n is 0. In other embodiments, n is 1.

Corroles for use in the invention are known in the art and are of the general formula:

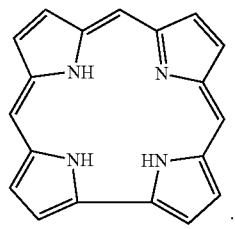

The corroles of the invention described herein can be attached to the M-OSO$_2$-moiety(ies) of the invention through any available carbon.

Particularly preferred corroles for use in the invention include those of the following general formula:

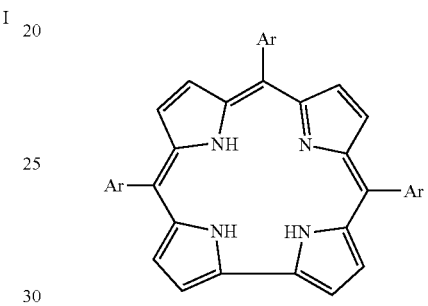

wherein Ar is an aryl group, for example, a phenyl or naphthyl group. In some embodiments of the invention, the aryl group is unsubstituted. In other embodiments, the aryl group is substituted. For example, when the aryl group is phenyl, the phenyl can be optionally substituted with halogen, for example, 1 to 5 halogen, that is, one or more of F, Cl, Br, or I, with F being a particularly preferred halogen. In exemplary embodiments, the aryl group is pentafluorophenyl. In other embodiments, when the aryl group is naphthyl, the naphthyl can be optionally substituted with 1 to 7 halogen, with F being a particularly preferred halogen.

Preferred corrolyls for use in the invention are those wherein Ar is pentafluorophenyl and include

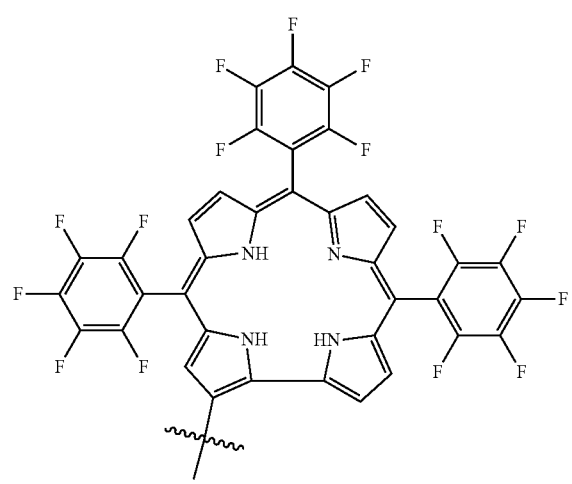

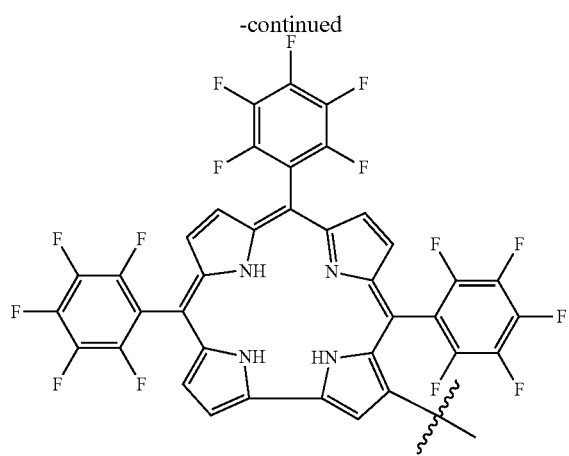

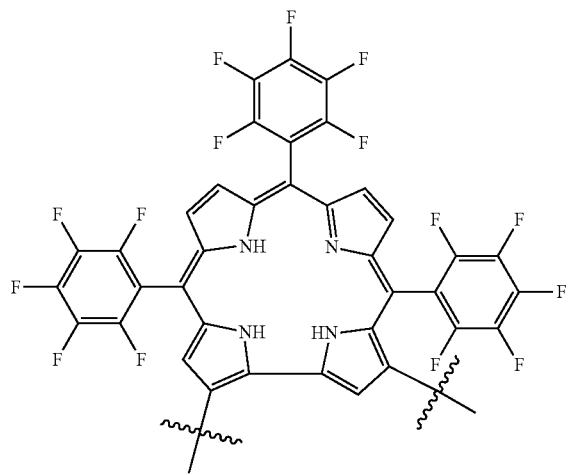

In addition to being substituted with one or more halogens, the aryl group can be further substituted with —NR³R⁴, wherein R³ and R⁴ are each independently H, $C_{1-10}$alkyl, $C_{1-10}$alkenyl, or -alkaryl; or R³ and R⁴, together with the nitrogen atom to which they are attached, form a heterocycloalkyl ring, which may be optionally substituted with $C_{1-6}$alkyl, for example, methyl or ethyl. Examples of —NR³R⁴ moieties include:

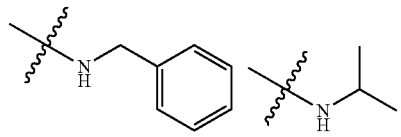

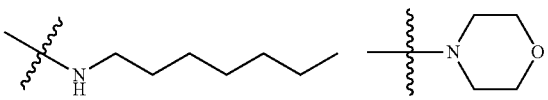

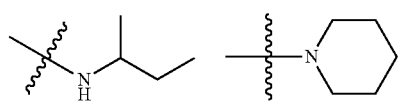

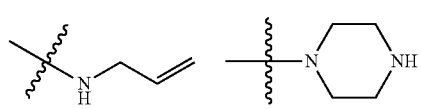

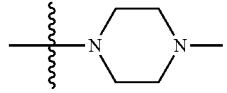

Corroles incorporating an —NR³R⁴ substituted aryl group can be accessed using methods known in the art, for example, using nucleophic substitution reactions. See, e.g., Hori, T., Osuka, A. Eur. J. Org. Chem. 2010, 2379-2386. For example, corroles incorporating an —NR³R⁴ substituted aryl group can be accessed using the following synthetic scheme:

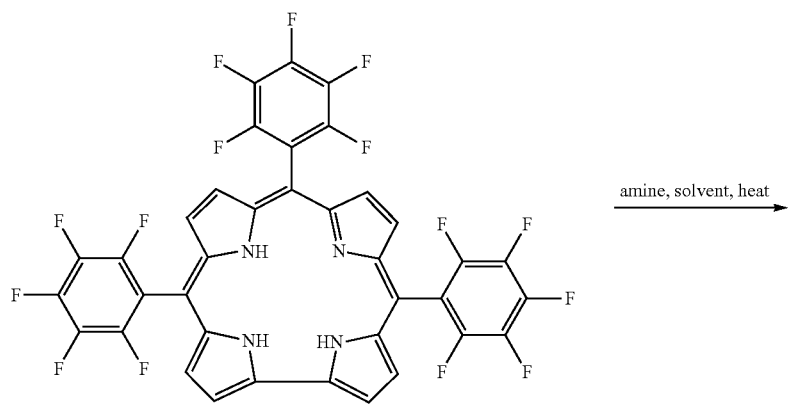

-continued

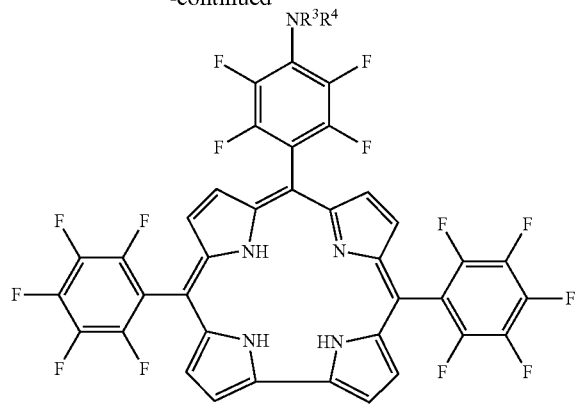

+

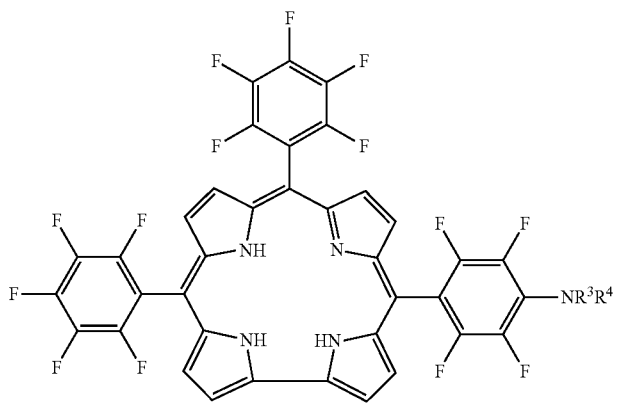

Amines that can be used in nucleophilic substitution reactions include, for example, benzylamine, octylamine, sec-butylamine, allylamine, dimethylamine, morphiline, piperidine, and N-methylpiperazine.

Another preferred corrole for use in the invention is of the general formula

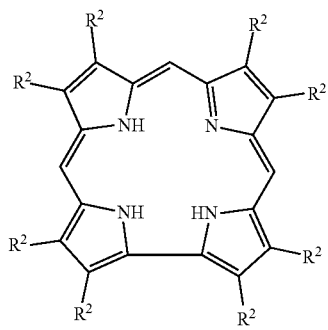

wherein each $R^2$ is independently H, $C_{1-6}$alkyl, halogen, or $M-O-SO_2-$, wherein M is as described above.

Yet another preferred corrole for use in the invention is of the general formula

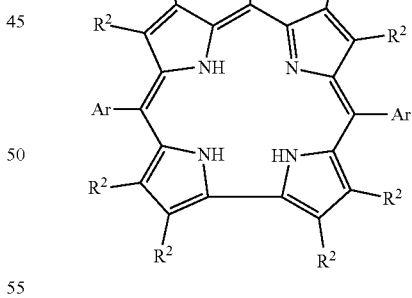

wherein Ar and $R^2$ are as previously described.

Corroles for use in the invention can also be metallated. In metallating a corrole, the nitrogens of the corrole are coordinated to a metal. Metals for use in the metallated corroles of the invention include any metal known in the art to be useful for coordinating to a corrole. Those of skill in the art understand that the function and use of the corrole can be modified by changing the coordinated metal.

For example, metals for use in metallating the corroles of the invention include Al, Ga, Fe, Mn, Sb, Co, Cr, Rh, Ru, Ro, Ir, V, Re, Cu, Sn, Ge, Ti, and Mo. Particularly preferred metals include Al and Ga. Another preferred metal is Fe. Yet another preferred metal is Mn. Another metal for use in the invention is Sb. Another metal for use in the invention is Co. Another metal for use in the invention is Cr. Another metal for use in the invention is Rh. Another metal for use in the invention is Ru. Another metal for use in the invention is Ro. Another metal for use in the invention is Ir. Another metal for use in the invention is V. Another metal for use in the invention is Re. Another metal for use in the invention is Cu. Another metal for use in the invention is Sn. Another metal for use in the invention is Ge. Another metal for use in the invention is Ti. Another metal for use in the invention is Mo.

The metals for use in metallating the corroles of the invention can be optionally coordinated to one or more ligands. Such ligands are known in the art and include, for example, pyridine, nitrosyl, imido, nitrido, oxo, ether, hydroxyl, chloride, carbonyl, fluoro, bromo, phenyl, iodo, phosphine, arsine, and the like. Those skilled in the art would readily be able to determine a suitable ligand for any particular metal. A particularly preferred ligand for use in the invention is pyridine. Preferred metal-ligand moieties include Al(ligand)$_2$ and Ga(ligand), with Al(pyridine)$_2$ and Ga(pyridine) being particularly preferred.

Exemplary materials of formula I according to the invention include:

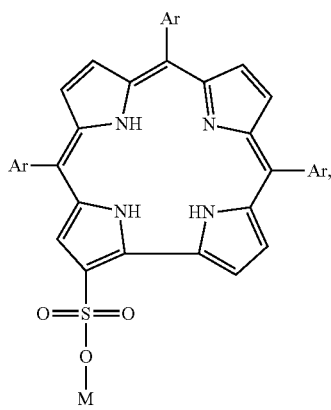

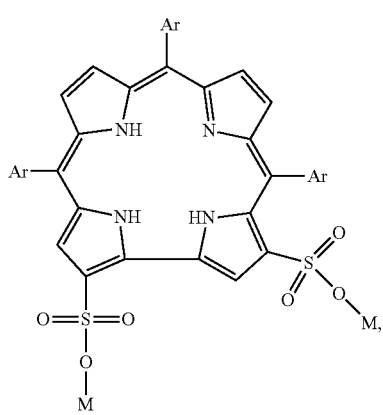

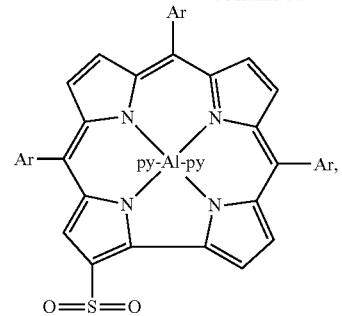

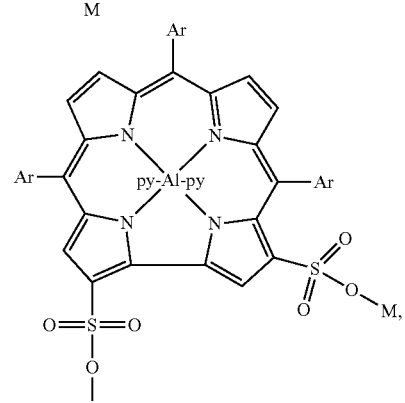

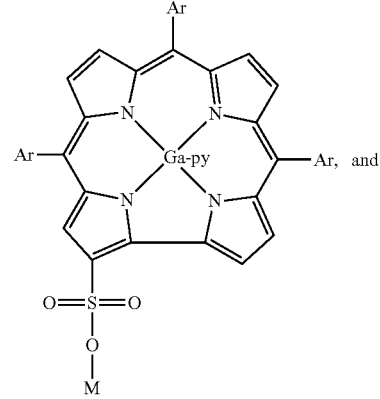

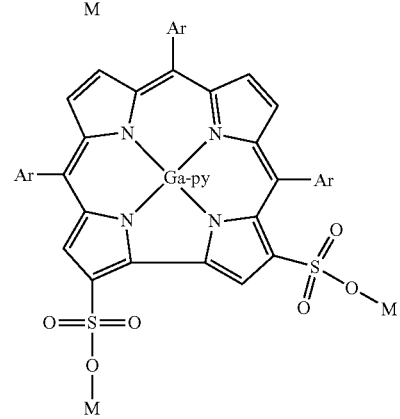

wherein Ar is pentafluorophenyl. In particularly preferred embodiments, Ar is pentafluorophenyl and M is TiO$_2$.

While 2,17 substituted corroles have been set forth herein, these examples are exemplary only and are not meant to limit the invention. It is envisioned that substitution at any position of the corrolyl or metallated corrolyl is within the scope of the invention.

Materials of formula I can be made according to the following method: contacting a surface comprising $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SnO_2$, $SiO_2$, or $ZnO$, the surface having at least one —OH group, with a compound of formula III:

$$(Cl-SO_2)_m\text{-}A \quad (III)$$

wherein A is corrolyl or metallated corrolyl; and
wherein m is 1 or 2.

Preferably, the synthetic methods of the invention are conducted in an organic solvent such as pyridine, with heat.

Compounds of formula III can be prepared according to methods known in the art. See, e.g., (a) Mahammed, A.; Goldberg, I.; Gross, Z. *Org. Lett.* 2001, 3, 3443. (b) Saltsman, I.; Mahammed, A.; Goldberg, I.; Tkachecko, E.; Botoshansky, M.; Gross, Z. *J. Am. Chem. Soc.* 2002, 124, 7411. See also, Blumenfeld, C. M.; Grubbs, R. H.; Moats, R. A.; Gray, H. B.; Sorasaenee, K. *Inorg. Chem.* 2013, 52, 4774. One exemplary method of preparing compounds of formula III is shown in Scheme 1.

The corrole or metallated corrole used in any of the methods of preparing materials of formula I can be any of the corroles or metallated corroles described herein.

In preferred methods of the invention, the surface is a nanoparticle surface. In other preferred methods of the invention, the surface comprises $TiO_2$.

Corrole coupling to the metal oxide surfaces of the invention can be performed by mixing metals of the invention bearing hydroxylated surfaces, preferably in nanocrystal form, with solutions of corrole and heating, preferably to reflux. After repeated washing with copious amounts of solvent such as, for example, $CH_2Cl_2$, acetone, and water, and drying under vacuum, powders are obtained.

Preferred corroles for use in the methods of making materials of formula I include:

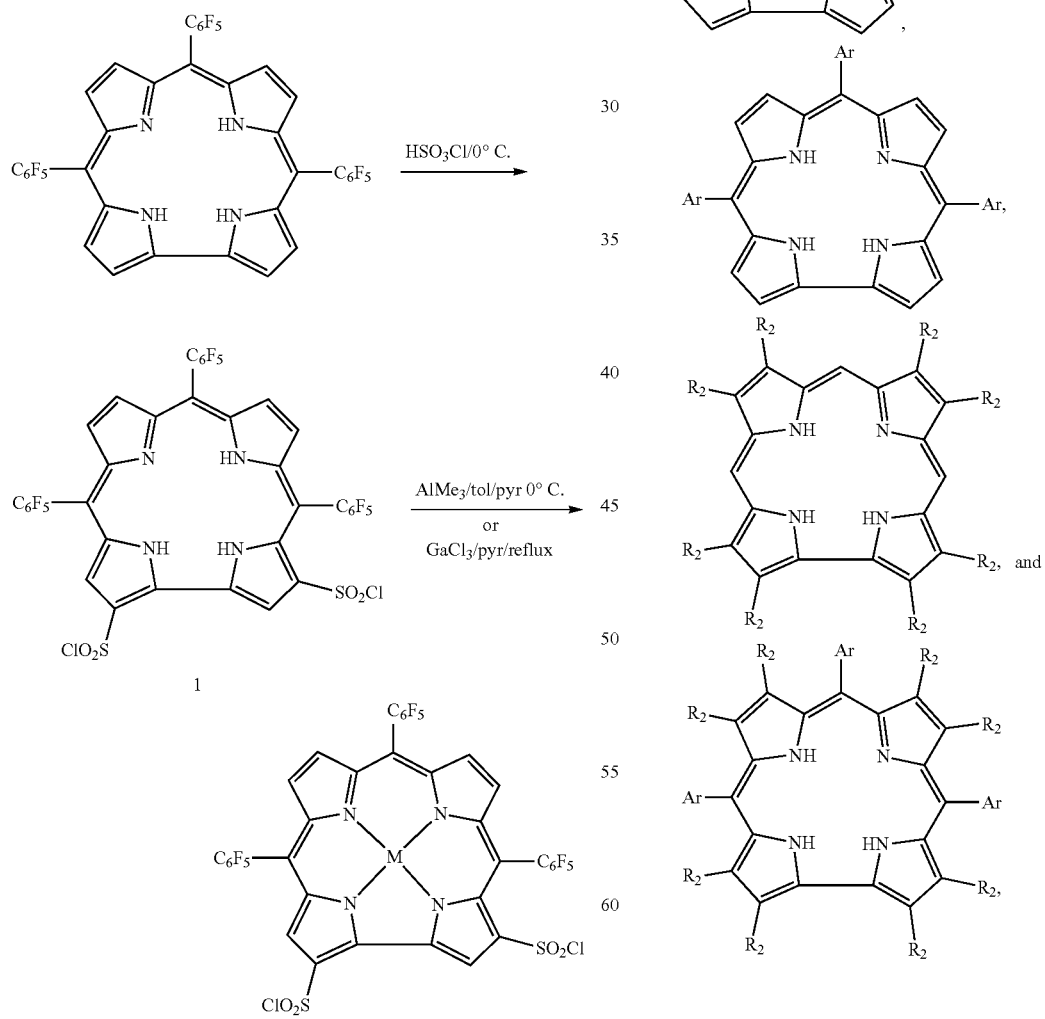

wherein Ar and $R^2$ are as set forth above.

Scheme 1

Preferred metallated corroles for use in the methods of the invention include:

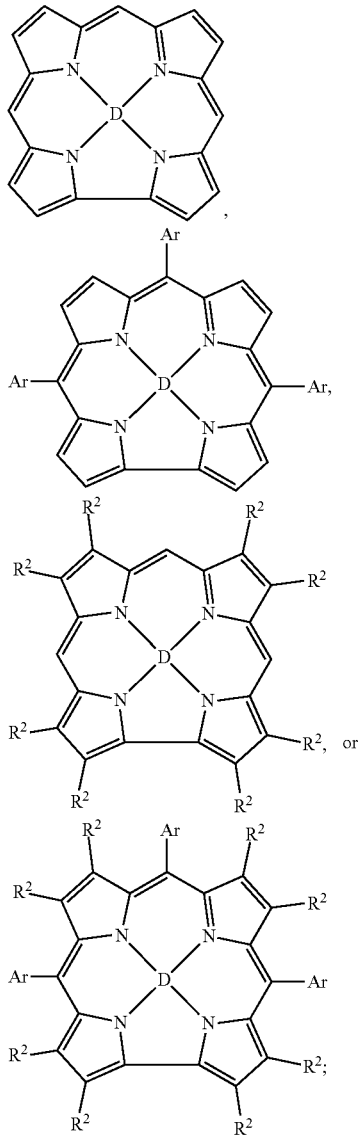

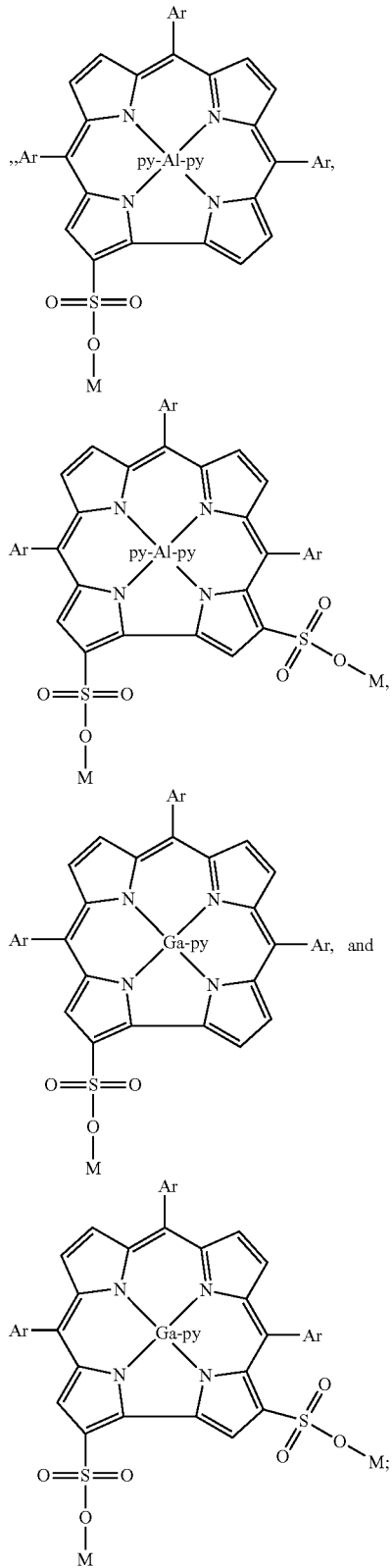

wherein Ar and $R^2$ are as set forth herein above and wherein D is Al, Ga, Fe, Mn, Sb, Co, Cr, Rh, Ru, Ro, Ir, V, Re, Cu, Sn, Ge, Ti, or Mo, each of which is optionally coordinated to one or more ligands. In preferred embodiments, D is Al(pyridine)$_2$ or Ga(pyridine).

The materials of the invention can be use in synthetic, biomedical, and optical imaging applications. In a preferred embodiment of the invention, the materials of formula I are used in imaging cancer in a patient. For example, a material according to formula I, wherein A is a metallated corrolyl, is administered to a patient. After a period of time sufficient for the material to be taken up by any cancer cells, the cancer cells within the patient are imaged using optical imaging, preferably using fluorescence imaging. Cancers that can be imaged using the methods of the invention will include glioblastoma, melanoma, breast cancer, liver cancer, and colon cancer.

Preferably, the materials used in the imaging methods of the invention include wherein Ar is pentafluorophenyl and M is preferably $TiO_2$.

The materials of formula I of the invention can also be useful in other fields of endeavor by changing the coordinating metal in the metallated corrole. For example, materials of the invention can be useful in the hydroxylation and hydroperoxidation of alkanes. The materials of the invention are also useful in epoxidation and sulfoxidation reactions. The materials of the invention are also useful in catalysis, for example, reduction and group transfer catalysis.

In other embodiments, the materials of formula I of the invention are useful in corrole-based sensing applications and dye-sensitized solar cells. In other embodiments, the materials of formula I of the invention will have anticancer activity or will prevent cell death. In other embodiments, the materials of the invention are useful in singlet oxygen sensitization. In other embodiments, the materials of the invention are useful in lipo-protein protection and neuroprotection.

The invention is also directed to materials according to formula II:

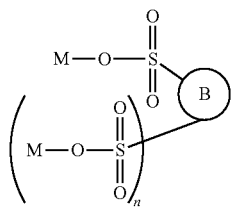

II wherein B is —NCO, $C_{1-10}$alkyl, or

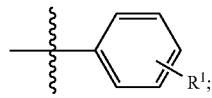

wherein $R^1$ is —COOH, —COOC$_{1-6}$alkyl, $C_{1-6}$alkyl, or aryl optionally substituted with halogen or $C_{1-6}$alkyl;

M is a surface comprising $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SnO_2$, $SiO_2$, or $ZnO$; and n is 0 or 1.

Within the scope of the invention, M is a surface that comprises a metal oxide, for example, a metal oxide that comprises at least one —OH group. The —OH group can be inherently present on the surface. Alternatively, the at least one —OH group can be incorporated by oxidizing the surface with a reagent such as hydrogen peroxide. Preferred surfaces for use in the invention include $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SnO_2$, $SiO_2$, and $ZnO$. In some embodiments, the surface comprises $TiO_2$. In some embodiments, the surface comprises $BaTiO_3$. In some embodiments, the surface comprises $SnO_2$. In some embodiments, the surface comprises $Al_2O_3$. In some embodiments, the surface comprises $Fe_2O_3$. In some embodiments, the surface comprises $Fe_3O_4$. In some embodiments, the surface comprises $ZrO_2$. In some embodiments, the surface comprises $CeO_2$. In some embodiments, the surface comprises $CdO$. In some embodiments, the surface comprises $Cr_2O_3$. In some embodiments, the surface comprises $CuO$. In some embodiments, the surface comprises $MnO$. In some embodiments, the surface comprises $Mn_2O_3$. In some embodiments, the surface comprises $MnO_2$. In some embodiments, the surface comprises $NiO$. In some embodiments, the surface comprises $SnO$. In some embodiments, the surface comprises $SnO_2$. In some embodiments, the surface comprises $SiO_2$. In some embodiments, the surface comprises $ZnO$.

In preferred embodiments, the surface is a nanoparticle surface.

In some embodiments, n is 0. In other embodiments, n is 1.

In certain embodiments, B is —NCO.

In other embodiments, B is $C_{1-10}$alkyl, for example methyl, ethyl, propyl, butyl, sec-butyl, tert-butyl, pentyl, and the like.

In yet other embodiments, B is

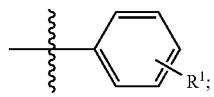

wherein $R^1$ is —COOH, —COOC$_{1-6}$alkyl; $C_{1-6}$alkyl; or aryl optionally substituted with halogen or $C_{1-6}$alkyl.

In some embodiments, B is

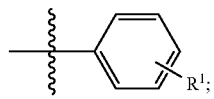

wherein $R^1$ is —COOH.

In other embodiments, B is

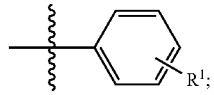

wherein $R^1$ is —COOC$_{1-6}$alkyl, for example, —COOMe, —COOEt, —COOPr, —COOBu, and the like.

In other embodiments, B is

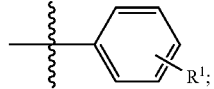

wherein $R^1$ is $C_{1-6}$alkyl, for example, methyl, ethyl, propyl, butyl, sec-butyl, tert-butyl, pentyl, and the like.

In yet other embodiments, B is

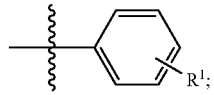

wherein $R^1$ is aryl, for example, phenyl or naphthyl. In these embodiments, the aryl can be optionally substituted with one or more substitutents selected from the group consisting of halogen and $C_{1-6}$alkyl.

In those embodiments wherein B is

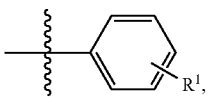

B is preferably

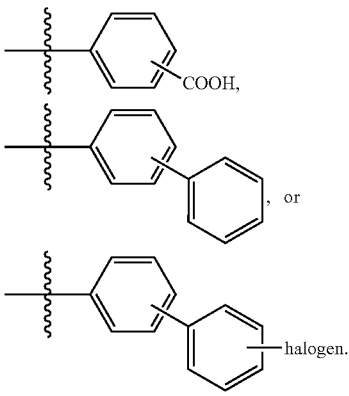

Methods of making materials of formula II are also within the scope of the invention. According to the invention, materials of formula II can be prepared by contacting a surface comprising $TiO_2$, $BaTiO_3$, $SnO_2$, $Al_2O_3$, $Fe_2O_3$, $Fe_3O_4$, $ZrO_2$, $CeO_2$, CdO, $Cr_2O_3$, CuO, MnO, $Mn_2O_3$, $MnO_2$, NiO, SnO, $SnO_2$, $SiO_2$, or ZnO, the surface having at least one —OH group, with a compound of formula IV:

wherein R is —NCO or

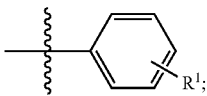

wherein $R^1$ is —C(O)OH, —C(O)O$C_{1-6}$alkyl; $C_{1-6}$alkyl; or aryl optionally substituted with halogen or $C_{1-6}$alkyl.

Compounds of formula IV can be prepared using methods known in the art.

Materials of formula II are useful in the field of chemical synthesis, for example, as catalysts. Materials of formula II are also useful in the field of material science.

As used herein, the term "halogen" refers to F, Cl, Br, or I.

As used herein, "alkyl" refers to branched or straight-chain saturated aliphatic hydrocarbon groups having the specified number of carbon atoms. For example, $C_{1-10}$alkyl denotes an alkyl group having 1 to 10 carbon atoms. Preferred alkyl groups include methyl, ethyl, propyl, butyl, sec-butyl, tert-butyl, pentyl, hexyl, and the like.

As used herein "alkenyl" refers to hydrocarbon chains that include one or more double bonds.

As used herein, "aryl" refers to phenyl or naphthyl.

As used herein, "alkaryl" refers to an aryl moiety attached through an alkylene group, for example, benzyl (—$CH_2$-phenyl).

As used herein, "heterocycloalkyl" refers to a 5 to 7-membered monocyclic or bicyclic saturated ring that includes at least one heteroatom that is N, O, or S. Examples include piperidinyl, piperazinyl, morpholinyl, and pyrrolidinyl.

As used herein, "corrolyl" refers to a corrole moiety.

The following examples are presented in order to more fully illustrate the preferred embodiments of the invention. They should in no way be construed, however, as limiting the broad scope of the invention.

EXPERIMENTAL SECTION

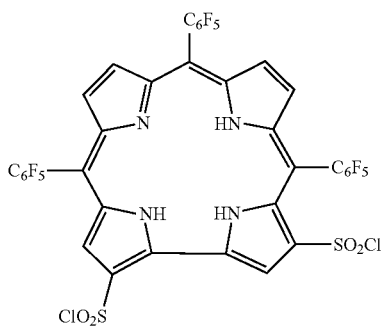

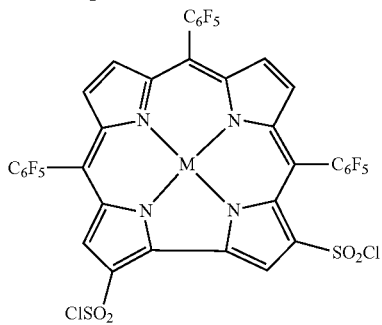

M = Al(py)$_2$ or Ga(py)
py = pyridine

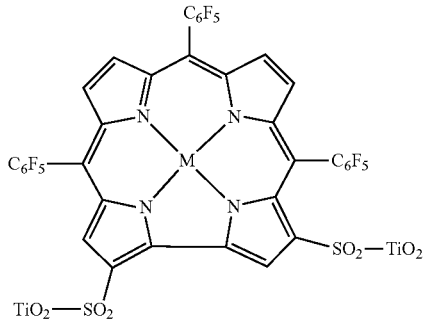

M = Al(py)$_2$ = 1-Al—TiO$_2$
Ga(py) = 1-Ga—TiO$_2$
py = pyridine

Materials.

2M AlMe$_3$ in toluene (Aldrich), GaCl$_3$ (Aldrich), HSO$_3$Cl (Aldrich), 21 nm nanopowder TiO$_2$ (Aldrich), 30% H$_2$O$_2$ (EMD) were obtained commercially and used as received. The starting material 5,10,15-tris(pentafluorophenyl)corrole (H$_3$tpfc) was prepared based on the literature method. The solvents pyridine and toluene were dried over a column. Acetone and dichloromethane used were both of reagent and spectroscopic grades depending on the applications. D-Luciferin potassium salt (Promega), Hoechst 34580 (Invitrogen™), Hoechst 33258 (Invitrogen™), Sytox Green (Invitrogen™), and FM® 1-43FX (Invitrogen™) were used as received according to the provider's instruction.

Chemical Preparation.

All preparations were carried out under Ar(g) atmosphere unless otherwise noted.

1. Corrole Preparation.

Preparation of 2,17-bischlorosulfonato-5,10,15-tris(pentafluorophenyl)corrole ($H_3$tpfc($SO_2$Cl)$_2$; 1) was performed according to the literature procedure. The metallocorroles described in this study were prepared in the following manner.

1.1. Preparation of 1-Al.

To the 20-mL toluene solution of 0.32 g of 1 (0.32 mmol) in a round bottom flask was added 0.8 mL of 2M AlMe$_3$ (1.6 mmol) in toluene solution at an icebath temperature. The solution was stirred for 10 min followed by the addition of 1 mL anhydrous pyridine. The solution was allowed to stir for another 10 min over ice. The reaction was quenched by an addition of ice chips. The dark green solution was then extracted with $CH_2Cl_2$ and washed with water. The solvent was removed in vacuo and the dry deep green solid was redissolved in $CH_2Cl_2$ followed by filtration. The filtrate was brought to dryness to afford the dark green solid (0.098 g, 26% yield). ESI-MS ($CH_2Cl_2$): m/z: 1014.87 [M-H]$^-$ (Calculated for $C_{37}H_6N_4F_{15}Cl_2S_2O_4Al$: 1015.88); $^1$H-NMR (400 MHz, acetone-d$_6$, ppm): δ=9.76 (s, 1H), 9.25 (s, 1H), 8.97 (d, 1H), 8.85 (d, 1H), 8.70 (d, 1H), 8.58 (d, 1H); $^{19}$F-NMR (376 MHz, acetone-d6, ppm): −138.7 (d, 4F), −140.0 (d, 2F), −156.9 (t, 1F), −157.5 (t, 1F), −158.1 (t, 1F), −164.9 (m, 2F), −165.3 (m, 2F), −167.0 (m, 2F); UV-Vis (toluene:pyridine, 95:5): λmax (ϵ M$^{-1}$ cm$^{-1}$)=436 (4.08×10$^4$), 625 (7.66×10$^3$) nm.

1.2. Preparation of 1-Ga.

To a heavy-walled Schlenk flask were added 0.20 g of 1 (0.20 mmol) and 0.57 g GaCl$_3$ (3.3 mmol) under Ar(g). The flask was chilled in N$_2$(l) and evacuated. 15 mL Degassed anhydrous pyridine (15 mL) was added to the flask via vacuum transfer. The flask was subsequently sealed and allowed to warm to room temperature. The reaction vessel was heated to 120° C. for 1 h. The pyridine solution was diluted with $CH_2Cl_2$ and washed with water three times. The solution was then filtered through glass wool and partially concentrated for recrystallization with hexanes overnight. The product was then filtered, dried, and washed with a combination of acetone, $CH_2Cl_2$, and toluene. This filtrate collected was brought to dryness in vacuo to afford a dark green solid (0.092 g, 38% yield). ESI-MS ($CH_2Cl_2$:pyridine): m/z: 1056.81 [M-H]$^-$ (Calculated for $C_{37}H_8N_4F_{15}Cl_2S_2O_4Ga$: 1057.82); $^1$H-NMR (500 MHz, CD$_2$Cl$_2$, ppm): δ=9.99 (s), 8.82 (m), 8.73 (m), 8.57 (m); $^{19}$F-NMR (376 MHz, acetone-d$_6$, ppm): −138.7 (d), −140.0 (d), −156.9 (t), −157.5 (t), −158.1 (t), −164.9 (m), −165.3 (m), −167.0 (m); UVVis (toluene:pyridine, 95:5): λmax (ϵ M$^{-1}$ cm$^{-1}$)=429 (1.65×10$^4$), 611 (5.61×10$^3$) nm.

2. TiO$_2$ Surface activation.

To the solid TiO2 nanoparticle (10 g) in a 2.0-L round bottom flask was added 1.2 L 30% H$_2$O$_2$ solution. The milky colloidal suspension was stirred under reflux or 5 h. Upon cooling, the off-white solid was isolated from the H$_2$O$_2$ solution by ultracentrifugation at 4° C. and washed with copious amount of water. The activated TiO$_2$ nanoparticle (TiO$_2$—OH) collected was dried in vacuo for 12 h and stored dry in a vial prior to use.

3. Surface Conjugation.

The following general procedure was employed for the conjugation of the corroles 1, 1-Al, and 1-Ga to the activated TiO$_2$ nanoparticle surface: To the mixed solids containing the activated TiO$_2$ and corrole in a 25-mL round bottom flask was charged with anhydrous pyridine. The suspension turned green immediately and was stirred under reflux before the reaction was stopped. The resulting green solid was isolated from the green solution by centrifugation and washed multiple times with dichloromethane, acetone, and deionized water until the centrifuge supernatant became colorless. The solid remained green, was dried in vacuo, and was stored until further use. The detailed preparation procedure for each corrole nanoconjugate is given as follows:

3.1. Preparation of 1-TiO$_2$.

To a 25 mL round bottom flask were added 0.32 g TiO$_2$—OH and 0.028 g of 1 (28.1 μmol), which was subsequently cycled with argon and vacuum. After establishment of the inert atmosphere, 8 mL anhydrous pyridine was added to the flask and the reaction was set to reflux for 2 h. The resulting green solid was collected in a manner following the general centrifugation and washing procedures outlined above.

3.2. Preparation of 1-Al—TiO$_2$.

To a 40 mL vial was added 1.18 g TiO$_2$—OH, which was subsequently cycled with argon and vacuum. To this flask, was added 5 mL anhydrous pyridine, followed by sonication to ensure even dispersion. In a second flask, was added 0.03 g of 1-Al (25.5 μmol) and 7 mL anhydrous pyridine under Ar(g). This solution was stirred and then added to the TiO$_2$—OH precursor via syringe. The reaction was sealed and allowed to reflux for 2 h after which, the resulting green solid was collected in a manner following the general centrifugation and washing procedures outlined above.

3.3. Preparation of 1-Ga—TiO$_2$.

To a 40 mL vial was added 0.84 g TiO$_2$—OH and 0.04 g of 1-Ga (32.8 μmol), which was subsequently cycled with argon and vacuum. After establishment of the inert atmosphere, 8 mL anhydrous pyridine was added to the flask and the reaction was set to reflux for 2 h. The resulting green solid was collected in a manner following the general centrifugation and washing procedures outlined above.

Spectroscopies.

UV-Vis spectra were either recorded on a Carey 50 spectrophotometer or a Hewlett-Packard 8453 diode-array spectrophotometer at room temperature from samples in various solvents. IR spectra were recorded with a SensIR Durascope ATR accessory plate on a Nicolet Magna-IR spectrometer, an uncooled pyroelectric deuterated triglycine sulfate (DTGS) etector, and a KBr beamsplitter. The $^1$H and $^{19}$F NMR spectra were recorded on a Varian Mercury 300 (300 MHz for 1H; 288 MHz for $^{19}$F) spectrometer. The NMR spectra were analyzed using MestReNova (v. 6.1.1). $^1$H NMR measurements were referenced to internal solvents. Fluorescence spectra were measured with a Jobin-Yvonne/SPEX Fluorolog spectrometer (Model FL3-11) equipped with a Hamamatsu R928 PMT. Samples were excited at λex=405-430 nm (the Soret region), 514 nm, and 600-630 nm (Q-band region) with 2-nm band-passes. The fluorescence was observed from λem=500-800 nm, depending on the excitation wavelength, at 2-nm intervals with 0.5 s integration times at room temperature.

Relative Fluorescence Quantum Yield Measurements.

The Φem measurements were performed using degassed toluene solutions of 1, 1-Al, 1-Ga, and tetraphenylporphyrin (as a standard). Samples were excited at λex=355 nm and the emission was observed from λem=500-800 nm. The standard tetraphenylporphyrin was excited at λex=514 nm and the emission was observed from λem=500-800 nm. Φem for tetraphenylporphyrin is 0.11.3 All relative fluorescence quantum yields were calculated based on the corresponding fluorescence spectra of the samples and the standard according to the equation:

$$\Phi_{em}(x) = \frac{A_s \cdot F_s \cdot \eta_x^2 \Phi_{em}(s)}{A_x \cdot F_s \cdot \eta_s^2}$$

where Φem(s) and Φem(x) are the relative fluorescence quantum yield of the standard and sample, respectively; As and Ax are the absorbance at the excitation wavelength for the standard and sample, respectively; Fs and Fx are the area under the corrected emission curve for the standard and sample, respectively; and ηs and ηx are the refractive index of the solvent used for the standard and sample, respectively.

Mass Spectrometry.

Samples were analyzed by direct infusion ESI in the negative ion mode using an LCT Premier XE (Waters) ESI-TOF mass spectrometer operated in the W configuration. The samples were prepared in $CH_2Cl_2$:isopropanol (9:1 v/v) at ≈10 µM and infused with an external syringe pump at 25 µL/min. Some samples contained 50 µL pyridine in 1 mL $CH_2Cl_2$:isopropanol mixture.

Surface Characterization.

X-ray photoelectron spectroscopy was performed on an M-Probe spectrometer that was interfaced to a computer running the ESCA2005 (Service Physics) software. The monochromatic X-ray source was the 1486.6 eV Al Kα line, directed at 35° to the sample surface. Emitted photoelectrons were collected by a hemispherical analyzer that was mounted at an angle of 35° with respect to the sample surface. Low-resolution survey spectra were acquired between binding energies of 1 and 1100 eV. Higher-resolution detailed scans, with a resolution of 0.8 eV, were collected on the F(1s) XPS line. All binding energies are reported in electronvolts.

Figure 8:
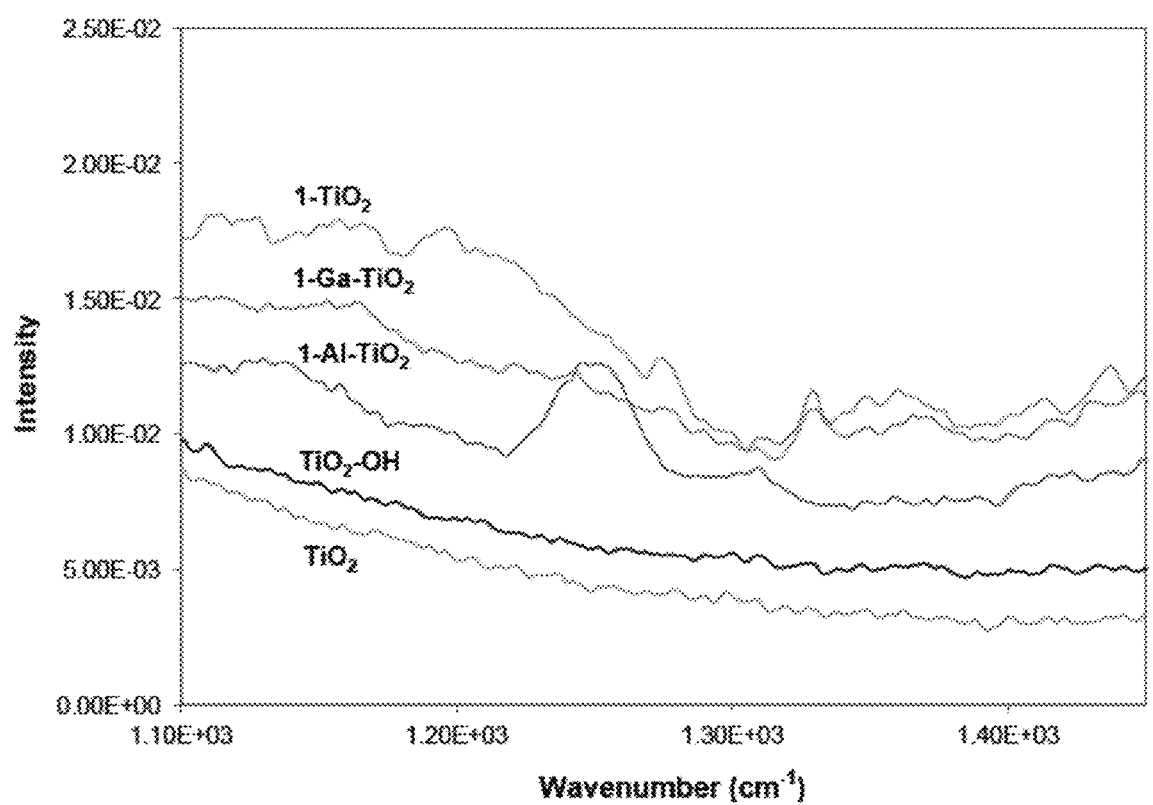
FIG. 8 depicts ATR-IR spectra for $TiO_2$ nanoparticles and preferred materials of the invention.
Figure 9:
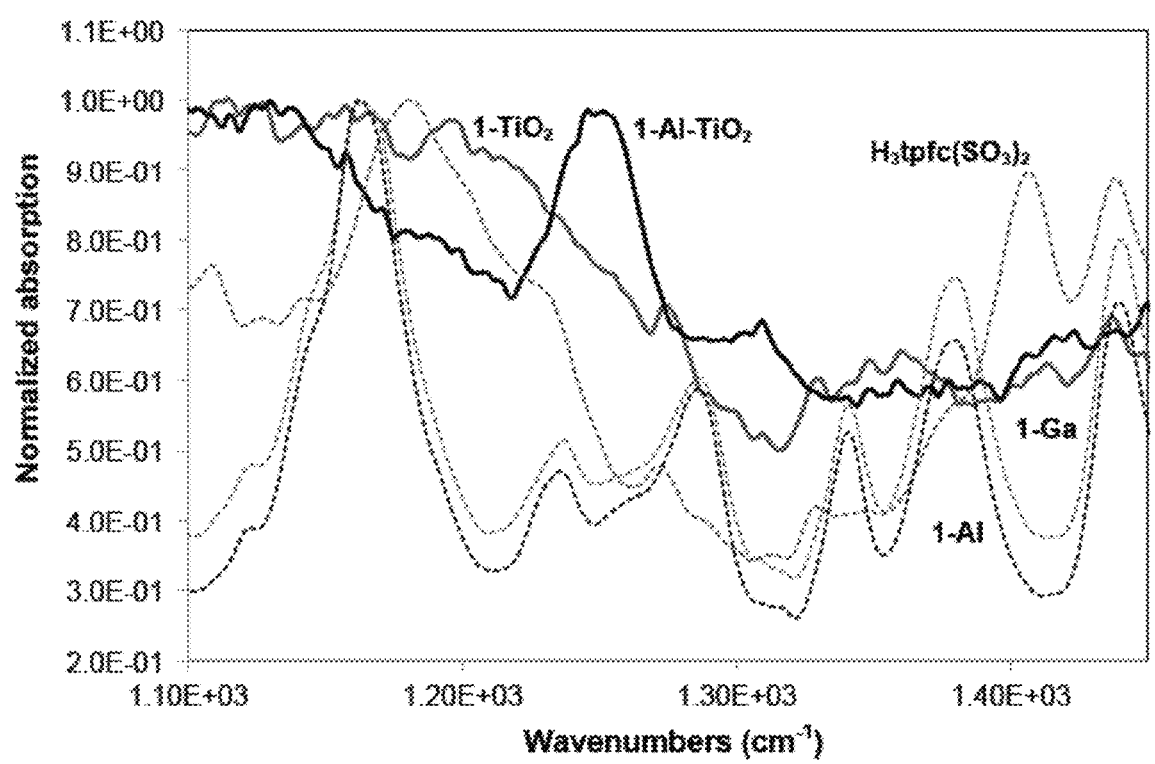
FIG. 9 depicts normalized ATR-IR spectra for $TiO_2$ nanoparticles and preferred materials of the invention.

Attenuated total reflectance (ATR) infrared spectra of powdered corrole-$TiO_2$ nanoconjugate samples were collected using a SensIR Durascope ATR accessory plate on a Nicolet Magna-IR spectrometer, an uncooled pyroelectric deuterated triglycine sulfate (DTGS) detector with a KBr window (400-4000 $cm^{-1}$), and a KBr beamsplitter. The spectral resolution was 4 $cm^{-1}$ and 64 scans were collected per spectrum. A KBr background spectrum was subtracted from the measured spectrum of the nanoconjugates to provide the desired FTIR characterization data. See FIGS. 8 and 9.

Confocal Microscopy.

The phantom imaging experiments were performed using a Zeiss LSM 710 Confocal Microscope (Carl Zeiss, Wake Forest, N.C.). The microscope system consists of a Zeiss 710 confocal scanner, 63×/1.4 Plan-APOCHROMAT oil immersion lens (Zeiss), Axio Observer Z1 microscope and diode-pump solid-state lasers. Two visible excitation lines (405 and 561 nm) were used for the experiments. The microscope is equipped with a QUASAR 32 channel spectral detector (two standard PMTs and a 32 channel PMT array) with spectral resolution of 9.7 nm. The software ZEN 2009 was used for hardware control. The laser power used for the experiments is 10% of the total available power (25 mW). ImageJ software was employed to process the resulting data.

Transmission Electron Microscopy.

The morphologies of the TiO2 nanoparticles before and after surface functionalization were imaged using a FEI Tecnai F30ST transmission electron microscope (TEM) operated at acceleration voltage of 300 kV. Images were recorded using a Gatan CCD camera. For TEM analysis, a small quantity of $TiO_2$ particles was dispersed in IPA by sonication. The dispersions were drop-cast onto C-Flat™ holey carbon films on a 200 mesh Cu TEM grid (purchased from Electron Microscopy Sciences).

Approximation of Loading of 1-Al on $TiO_2$ Surface.

Calculation of the corrole 1-Al's loading on the surface of $TiO_2$ was based on the absorbance values obtained from the integrated sphere electronic absorption measurements described as follows.

Absorption Spectroscopy.

Figure 3:
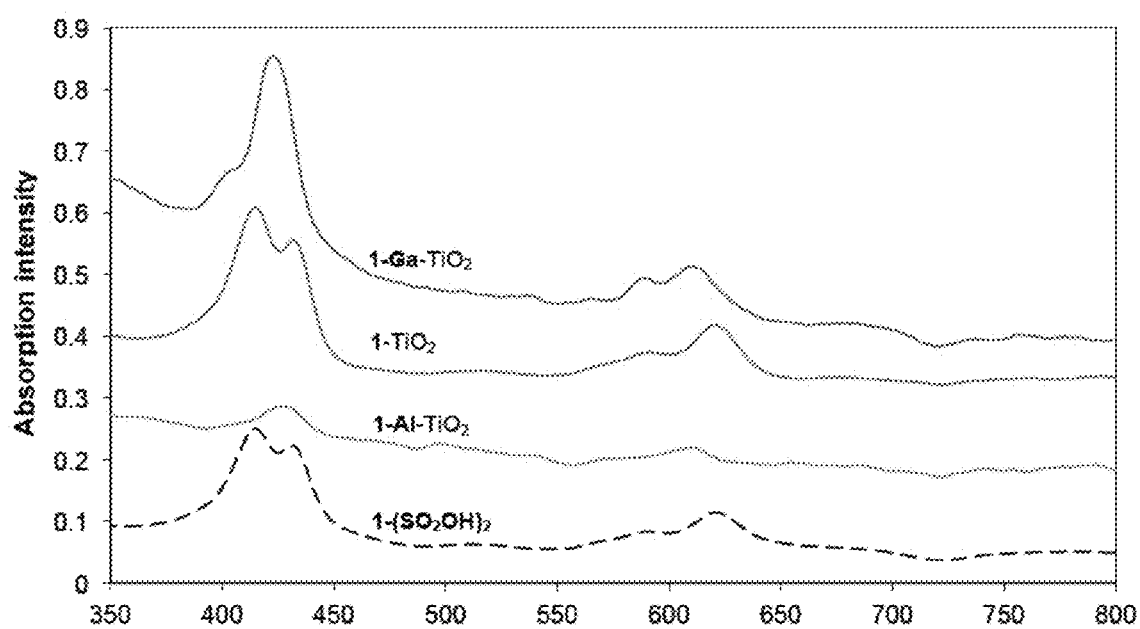
FIG. 3 depicts electronic absorption spectra for an amphiphilic corrole ($H_3$tpfc($SO_2$OH)$_2$) and corrole-$TiO_2$ nanoconjates of the invention in phosphate buffer saline pH 7.4.

Thin film transflectance measurements were used to calculate the dye loading on the $TiO_2$ nanoparticles. Both peroxide-etched and dye-functionalized nanoparticles were dispersed in a polydimethylsiloxane (PDMS) polymer matrix. The weights of the $TiO_2$ nanoparticles, PDMS base (Sylgard® 184 silicone elastomer base from Dow Corning), and curing agent (Sylgard® 184 silicone elastomer curing agent from Dow Corning) are provided in Table 1 below. The nanoparticles were first dispersed in a minimal amount of isopropanol (IPA) by sonication. The dispersion of $TiO_2$ nanoparticles in IPA was then mixed with the PDMS base and curing agent using a Vortex mixer. The mixtures were cast into films onto quartz substrates and allowed to cure in air for 12 hours followed by curing in a drying oven at 60° for 2 hours. See FIG. 3.

TABLE 1

Weights of $TiO_2$ nanoparticles, weights of the PDMS base and curing agnet used to case PDMS films, weight % $TiO_2$ in the films, film weight, and mass of $TiO_2$ per volume of PDMS.

| Sample | Mass $TiO_2$ (mg) | Mass IPA (g) | Mass PDMS base (g) | Mass PDMS curing agent (g) | Total weight (g) | Est. dry film weight (g)[a] | Weight % $TiO_2$ | Film weight (g) | Mass $TiO_2$/ volume PDMS (g/L)[b] |
|---|---|---|---|---|---|---|---|---|---|
| Etched $TiO_2$ | 3.35 | 3.683 | 0.9266 | 0.1220 | 1.4203 | 1.0593 | 0.32 | 0.2901 | 3.3 |
| 1-Al—$TiO_2$ | 3.25 | 3.234 | 0.9425 | 0.1154 | 1.3846 | 1.0676 | 0.30 | 0.3384 | 3.2 |

[a]Separate measurements showed that 98% of the IPA evaporated during curing of the PDMS film.
[b]A value of 0.965 g/cm³ was used for the density of PDMS.

Transflectance spectra of the etched and dye-functionalized $TiO_2$ nanoparticle films were measured using a Cary 5000 UV-Vis-NIR spectrometer from Agilent Technologies equipped with an integrating sphere (External DRA 1800), a PMT detector, a quartz-iodine lamp for the visible region (350-800 nm), and a deuterium lamp for the ultraviolet region (300-350 nm). Because the $TiO_2$ nanoparticles cause diffuse scattering of the incident illumination, the PDMS films were placed in the center of the integrating sphere such that both the transmitted, T, and the reflected, R, (including the spectrally reflected and diffusely scattered light) light were collected by the PMT detector. The transflectance measurements allow for the absorbance, A, of the films to be determined by A=−log(T+R). The concentration, C, of the dye within the PDMS films was then calculated using the Beer-Lambert law, A=εCl, where ε is the extinction coefficient of the dye and l is the film thickness (determined by profilometry, see below). The absorbance values at 426 and 595 nm (corresponding to the Soret and Q bands of the dye, respectively) for the PDMS film containing the dye-functionalized $TiO_2$ nanoparticles, the estimated extinction coefficients of the dye at these wavelengths, and the film thicknesses are provided in Table 2 below. The absorbance values for the PDMS film containing the unfunctionalized, peroxide-etched $TiO_2$ nanoparticles at these wavelengths are also provided, which were subtracted from the absorbance values of the dye-functionalized $TiO_2$ nanoparticles. The dyeloading was determined to be between 2.3 and 3.5 μmole of dye per grams of $TiO_2$ (based on whether the Soret or Q band was used to determine the dye concentration).

for each well is 300 μL. After treatment, the treated cells and controls were incubated in the dark in 5% $CO_2$ at 37° C. for a period of 24, 48, and 72 h. The cells were imaged using the cooled IVIS® animal imaging system (Xenogen, Alameda, Calif. USA) linked to a PC running with Living Image™ software (Xenogen) along with IGOR (Wavemetrics, Seattle, Wash., USA) under Microsoft® Windows® 2000. This system yields high signal-to-noise images of luciferase signals emerging from the cells. Before imaging, 0.5 mL of 150 mg/mL luciferin in normal saline was added to each well. An integration time of 1 min with binning of 5 min was used for luminescent image acquisition. The signal intensity was quantified as the flux of all detected photon counts within each well using the LivingImage software package. All experiments were performed in triplicate.

For PMH cell culture experiments, the cells were plated in a 6-chamber slide (Cultureslide, BD). After three hours, media was exchanged (DMEM-F12) and the cells were treated with 1-Al—$TiO_2$ suspended in PBS over a range of 0.3 ng/mL to 0.3 mg/mL. A primary stock solution (6.3 mg 1-Al—$TiO_2$ in 1 mL PBS) was prepared. The primary stock solution was further diluted to prepare secondary and ter-

TABLE 2

Absorption values at 426 and 595 nm and thicknesses for PDMS films containing dyefunctionalized and peroxide-etched $TiO_2$ nanoparticles, and estimated dye loading of the $TiO_2$ particles based on absorption measurements.

| Wavelength (nm) | Dye-functionalized $TiO_2$ absorbance | Film thickness (cm) | Est. dye extinction coefficient $(M^{-1}cm^{-1})^a$ | Etched $TiO_2$ absorbance | Film thickness (cm) | Dye concentration (M) | Dye loading (μmoles of dye/g of $TiO_2$) |
|---|---|---|---|---|---|---|---|
| 426 | 0.170 | 0.054 | $4.08 \times 10^4$ | 0.005 | 0.054 | $7.5 \times 10^{-5}$ | 2.3 |
| 595 | 0.048 | 0.054 | $7.66 \times 10^3$ | 0.002 | 0.054 | $1.1 \times 10^{-4}$ | 3.5 |

$^a$Extinction coefficients measured in toluene:pyridine (95:5) mixture.

Profilometry.

Thickness profiles of the PDMS films were measured using a Bruker DektakXT stylus surface profilometer. The diameter of the diamond-tipped stylus was 2 μm and a weight of 1 mg was applied to the film, respectively. The stylus was scanned at a rate of 250 μm/s. The thickness profiles were used measure the average path length through the PDMS films during the transflectance measurements.

Cell Culture and Cell Viability Assay.

Pathogen-free U87-LUC cell line (TSRI Small Animal Imaging and Research Laboratory) was grown in 75 mL flask in Dulbecco's Minumal Essential Medium (DMEM) in 5% $CO_2$ at 37° C. The cell culture medium was supplemented with 10% fetal bovine serum (FBS) and 1% the antibiotic primocin. The cell culture medium was replenished every two days and the cells were passaged once they reached 80% confluence. Primary mouse hepatocytes (PMH) were isolated and cultured as previously described.

For U87-Luc cell culture experiments. The cells were plated in an 8-chamber slide (Cultureslide, BD) were treated with 1-Al—TiO2 suspended in PBS over a range of 2 ng/mL to 2 mg/mL. A primary stock solution (6.3 mg 1-Al—$TiO_2$ in 1 mL PBS) was prepared. The primary stock solution was further diluted to prepare secondary and tertiary stock solutions. The various amount of stock solutions were added to the eight-well glass slide plated with cells to give the aforementioned range of concentrations. The final volume for each well is 2000 μL. After 24 or 48 h of treatment, cells were double stained with Hoechst 33258 (8 mg/mL) and Sytox Green (1 mmol/L). Quantitation of total and necrotic cells (Sytox Green positive) was performed by counting cells in at least 5 different fields using ImageJ, as previously described. All experiments were done in triplicate.

In Vitro Confocal Fluorescence Microscopy.

The U87-Luc cells were seeded at 20,000 cells per well on an 8-chamber slide (Cultureslide, BD) and allowed to grow overnight. Cells were washed with PBS and were incubated in serum free media mixed 1:1 with 1-Al—$TiO_2$ for 24, 48, and 72 h at 37° C. over the concentration range similar to the U87-Luc cell viability assay (2 ng/mL to 2 mg/mL). Cells were then washed 3× with PBS and stained with Hoechst 33258 and FM® 1-43FX stains. The cells were chilled on iced and then imaged without being fixed using a Zeiss LSM 710 inverted confocal microscope.

Electronic absorption spectra for 1,1-Al, and 1-Ga was obtained in degassed toluene. Solutions reveal the signature Soret and Q-bands for these tetrapyrrolic macrocycles (FIG. 1). The electronic absorption data for the chlorosulfonated corroles are also given in Table 3.

TABLE 3

Electronic spectroscopic data for chlorosulfonated corroles 1, 1-Al, and 1-Ga in toluene solution

| Corrole | Electronic Absorption[a] $\lambda_{max}$[b] (nm) | Fluorescence[a] $\lambda_{ex}$ (nm) | $\lambda_{ex}$ (nm) | $\phi_{em}$[c] |
|---|---|---|---|---|
| 1 | 430 (S) 580 (Q) | 426 | 670 | 0.094 |
| 1-Al | 424 (S) 592 (Q) | 420 | 611 | 0.127 |
| 1-Ga | 426 (S) 588 (Q) | 427 | 609 | 0.099 |

[a]The measurements were performed in degassed toluene.
[b]The maximum absorption wavelengths are reported for both Soret (S) and Q-bands (Q).
[c]The relative emission quantum yields were determined using tetraphenylporphyrin as a standard.

The electronic absorption spectra of the colloidal suspensions of 1-TiO$_2$, 1-Al—TiO$_2$, and 1-Ga—TiO$_2$ nanoconjugates in PBS pH 7.4 reveal maximum absorptions centered around 425 and 600 nm for the Soret and Q-bands, respectively (Table 4).

TABLE 4

Electronic absorption, vibrational, and X-ray photoelectron spectroscopic data for corrole-TiO$_2$ nanoconjugates 1-TiO$_2$, 1-Al—TiO$_2$, and 1-Ga—TiO$_2$

| Conjugate | Electronic Absorption $\lambda_{max}$ (nm) | SO$_2$ Vibrational Frequency (cm$^{-1}$) Sym | Asym | F(1s) Binding Energy (eV) |
|---|---|---|---|---|
| 1-TiO$_2$ | 415, 430 (S) 591, 621 (Q) | 1153 | 1410 | 691 |
| 1-Al—TiO$_2$ | 427 (S) 576, 610 (Q) | 1244 | 1431 | 690 |
| 1-Ga—TiO$_2$ | 423 (S) 589, 610 (Q) | 1160 | 1450 | 688 |

These peak maxima are in agreement with the spectroscopic properties of the corresponding molecular corrole (Table 3). The Soret band splitting for 1-TiO$_2$ is similar to the splitting observed for its amphiphilic molecular counterpart 2,17-bissulfonato-5,10,15-tris(pentafluorophenyl) corrole in an aqueous solution at physiologic pH, supporting the presence of the sulfonate linkage on the corrole anchored to TiO$_2$ surfaces. The splitting pattern, however, was not observed for the metalloconjugates 1-Al—TiO$_2$ and 1-Ga—TiO$_2$, owning to the presence of metal bound to deprotonated nitrogen atoms.

Figure 10:
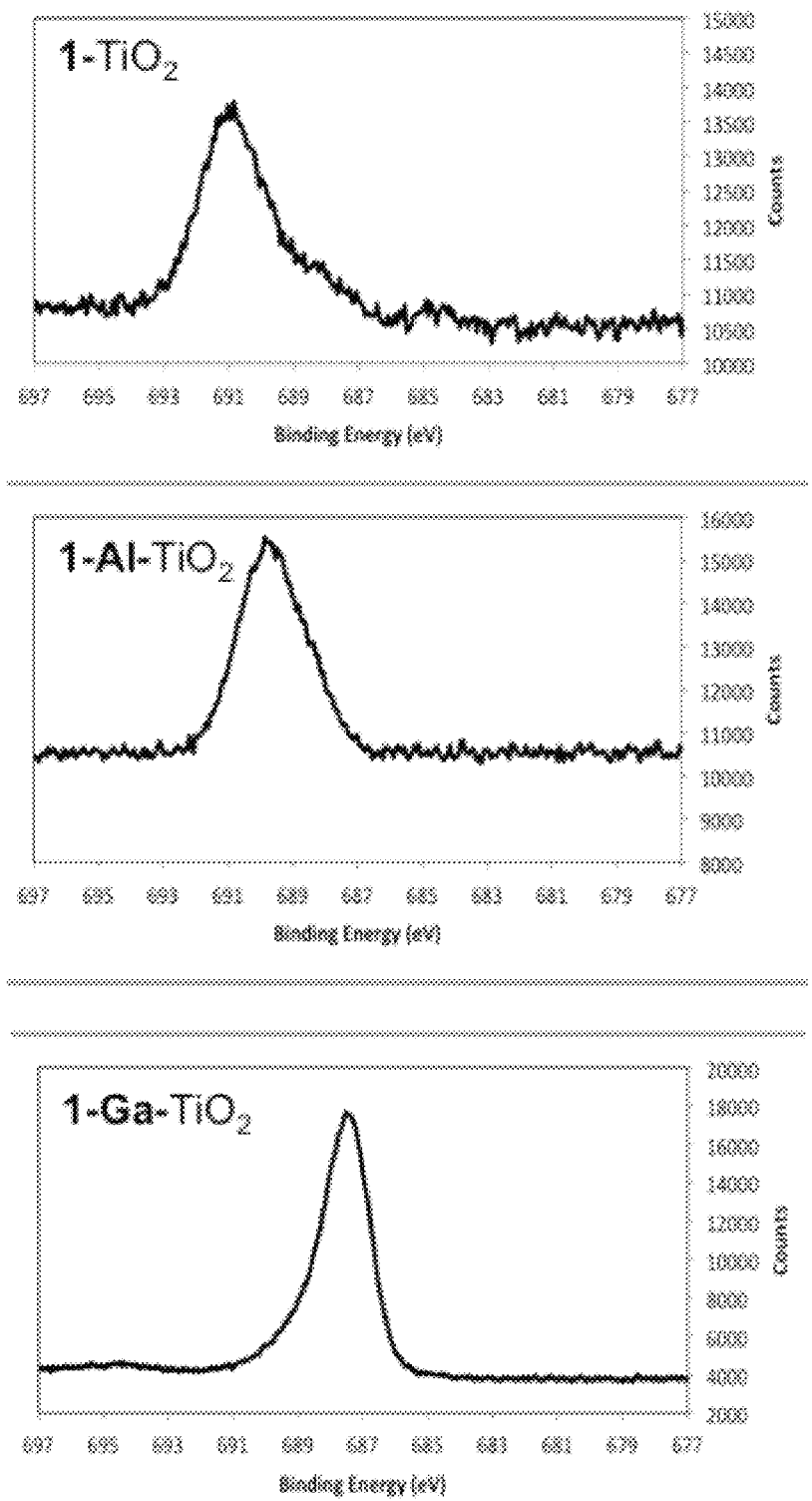
FIG. 10 depicts X-ray photoelectron spectra for nanoconjugates 1-TiO$_2$, 1-Al—TiO$_2$, and 1-Ga—TiO$_2$ exhibiting the F(1s) band.

Characterization of the fine green powder of 1-TiO$_2$, 1-Al—TiO$_2$, and 1-Ga—TiO$_2$ with FT-IR spectroscopy reveals vibrational absorption bands around 1180-1250 cm$^{-1}$ assigned to the symmetric stretching of SO$_2$ groups as well as those around 1400-1450 cm$^{-1}$ assigned to asymmetric stretching of SO$_2$ groups of covalent sulfonates. The presence of these vibrational signatures suggests that the corroles are covalently attached to the surface of TiO$_2$ through a sulfonate linkage. The vibrational frequencies for these TiO$_2$-corrole nanoconjugates are listed in Table 2. X-ray photoelectron spectroscopy was performed to study the elemental presence of the surface of the nanoparticle conjugates (Table 4). High-resolution scans for the spectra of the conjugates revealed F(1s) binding energy peaks between 688 and 691 eV, suggesting the presence of corresponding pentafluorophenyl corroles attached to the TiO$_2$ surface. See FIG. 10.

Confocal fluorescence microscopy images of aggregates of the nanoconjugates 1-TiO$_2$, 1-Al—TiO$_2$, and 1-Ga—TiO$_2$ in the solid state (FIG. 1) were taken with the samples illuminated at $\lambda_{ex}$=405 nm and the $\lambda_{em}$ recorded from 508 to 722 nm. The images for 1-Al—TiO$_2$ and 1-Ga—TiO$_2$ (FIGS. 1e and 1h) exhibit fluorescence areas on the nanoparticles compared to the relatively darker image for 1-TiO$_2$. The fluorescence signals observed with various intensities across the TiO$_2$ samples for 1-Al—TiO$_2$ and 1-Ga—TiO$_2$ also suggest that the TiO$_2$ surfaces are not evenly functionalized because of material aggregation. Selected fluorescence areas (white circles) on all three images, spectral profiles representing the nanoconjugates 1-TiO$_2$, 1-Al—TiO$_2$, and 1-Ga—TiO$_2$ were obtained (FIGS. 1c, 1f, and 1i). These spectral profiles and fluorescence signal intensities are in agreement with the fluorescence spectra (FIGS. 1a, 1d, and 1g) obtained from the molecular corroles 1, 1-Al, and 1-Ga.

Figure 2:
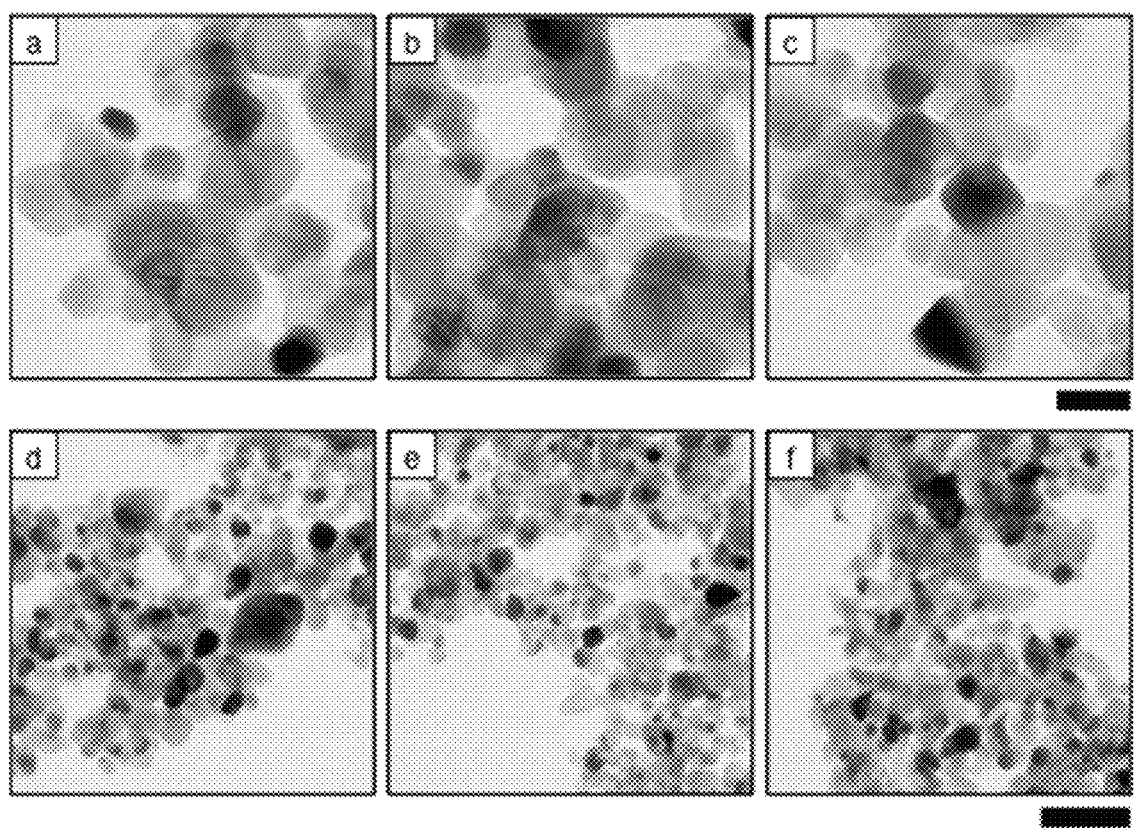
FIG. 2 depicts transmission electron microscopic (TEM) images of $TiO_2$ nanoparticles of the invention before and after dye-functionalization. (a and d) Images of the initial $TiO_2$ nanoparticles. (b and e) Images of the nanoparticles after peroxide-etching. (c and f) Images of the nanoparticles after dye functionalization. The scale bar is 25 nm for the top row and 100 nm for the bottom row of images.

The nanoconjugate 1-Al—TiO$_2$ was chosen as a candidate for cellular uptake and cytotoxic effect studies. The TEM images of TiO$_2$ (FIG. 2) show the average particle size to be 29 nm, post-corrole functionalization, albeit, they appear to aggregate. Images were taken for both before and after surface functionalization as well as for both before and after H$_2$O$_2$-etching. Absorption measurements of the particles embedded in a transparent polymer matrix, facilitated with the use of an integrating sphere, indicate nearly identical absorption features in the molecular and conjugated species. These experiments afforded an approximate loading of 1-Al on the surfaces of ca. 10-40 mg/g TiO$_2$. (FIG. 2).

Figure 4:
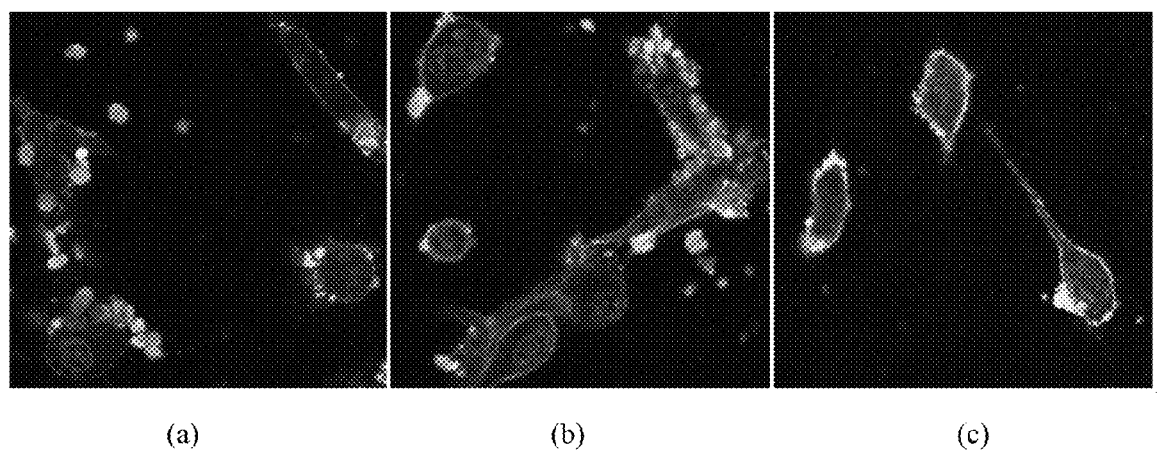
FIG. 4 depicts confocal fluorescence microscopic images of U87-Luc cells treated with 0.2 μg/mL of a preferred embodiment of the invention (1-Al—$TiO_2$) after 24 h (a), 48 h (b), and 72 h (c).

Treatment of the luciferase-transfected glioblastoma cell U87-Luc with a wide range of 1-Al—TiO$_2$ concentrations (2 ng/mL to 2 mg/mL) reveals internalization of these nanocojugates over a period of 24, 48, and 72 h as shown by the confocal fluorescence microscopic (CFM) images (FIG. 4).

The CFM images were taken after the cells were stained with the nuclear and cell membrane dyes, and washed with the media solution several times to remove the excess dyes and 1-Al—TiO2 nanoconjugates. The nucleus labeled with a Hoechst stain is seen in bluish purple ($\lambda$ex=405 nm, $\lambda$em=460 nm). The membrane seen in green is labeled with the dye FM® 1-43FX ($\lambda$ex=488 nm, $\lambda$em=580 nm). The nanoconjugate 1-Al—TiO$_2$ is observed in red ($\lambda$ex=405 nm, $\lambda$em=634 nm).

Figure 5:
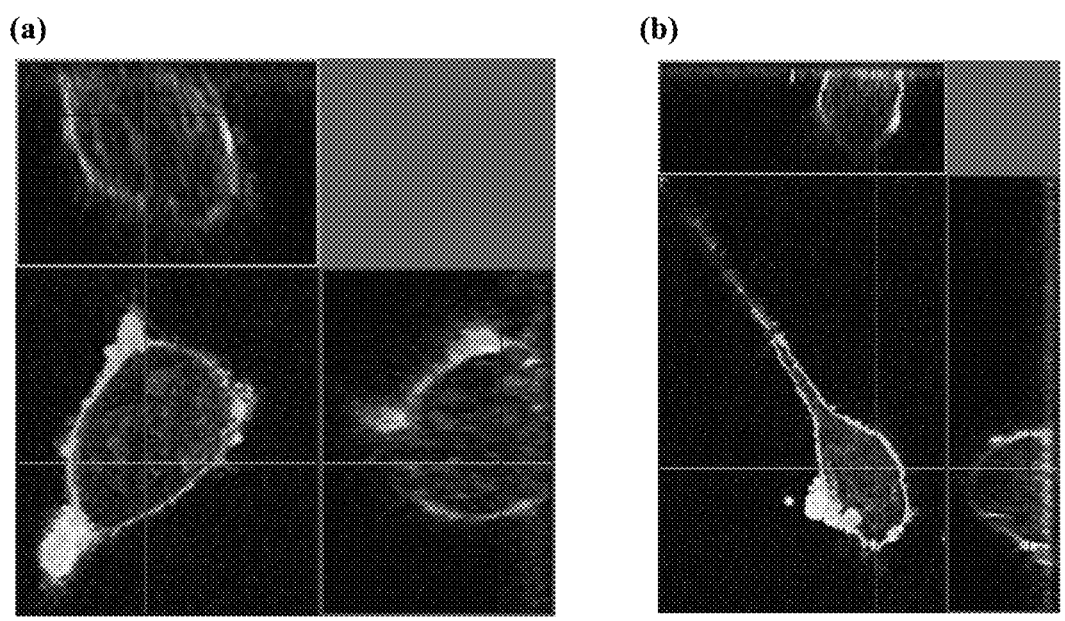
FIG. 5 depicts Z-stacked confocal fluorescence micrographic images of individual U87-Luc cells taken at 0.5-μm slice intervals after (a) 48 h and (b) 72 h of treatment with 0.2 μg/mL of a preferred embodiment of the invention (1-Al—$TiO_2$).

The Z-stacked confocal fluorescence microscopic (CFM) images (FIG. 5) of U87-Luc cells treated with similar concentrations (2 ng/mL to 2 mg/mL) of 1-Al—TiO$_2$ for 48 and 72 h from three different perspectives are also shown (FIG. 5). The Z-stacked CFM images of individual cells were taken at 0.5-1 μm slice intervals from top to bottom.

The 1-Al—TiO$_2$ nanoconstruct could also be internalized through endocytosis. Based on the confocal fluorescence images, the nanomaterials 1-Al-modified TiO$_2$ is suspended in the cytosol as opposed to the modified TiO$_2$ labeled with alizarin red S, which showed perinuclear localization in HeLa cells. These findings suggest a distribution pattern of the TiO$_2$ nanoconjugates within the cells similar to another study, in which 1-D TiO$_2$ nanorods and nanoparticles labeled with fluorescein thiocyanate were internalized into HeLa cells after a given period of time. The internalization of 1-Al—TiO$_2$ into glioblastoma cells can also be observed even at a very low concentration range (<μg/mL).

Figure 6:
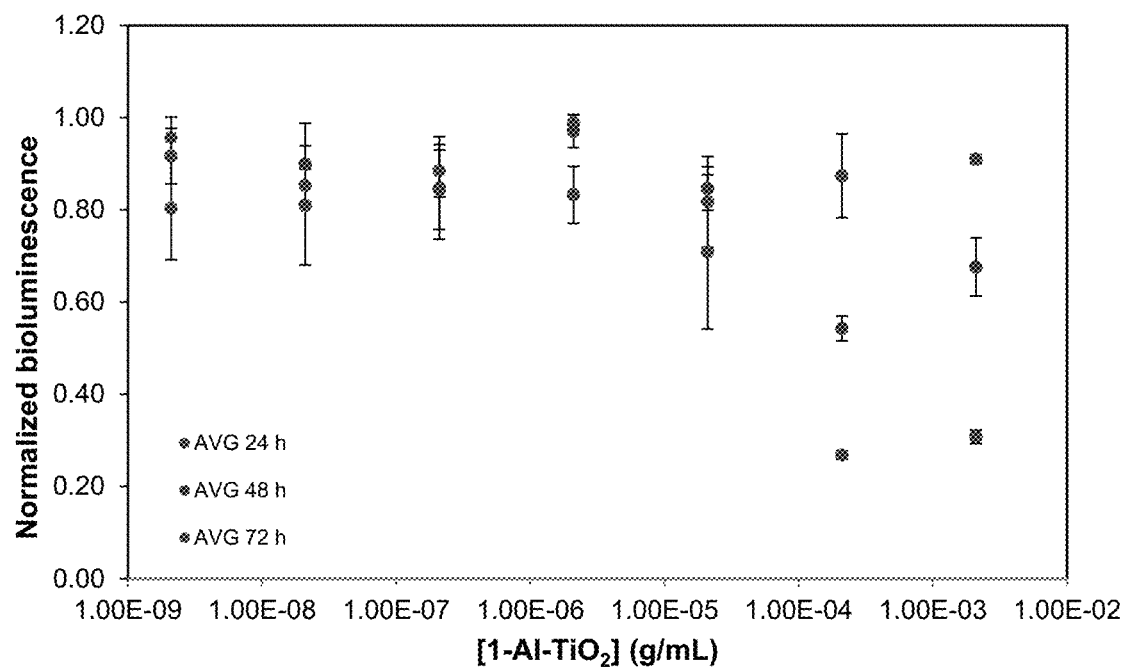
FIG. 6 depicts a cell viability plot of U87-Luc cells treated by of a preferred embodiment of the invention (1-Al—$TiO_2$) at various concentrations (2 ng/mL to 2 mg/mL) using a bioluminescence assay.

TiO$_2$ nanoparticles exhibit various degrees of cytotoxic activities upon photoactivation by UV-Vis light leading to formation of reactive oxygen species. To best study and understand the cytotoxic effect of the 1-Al—TiO$_2$ conjugate that is not related to the photocatalytic property of TiO$_2$ on cell death, the glioblastoma cell U87-Luc was treated in the absence of UV-Vis irradiation with the same range of 1-Al—$TiO_2$ concentrations (2 ng/mL to 2 mg/mL) as in the cell internalization studies. The cells were incubated over a period of 24, 48, and 72 h prior to bioluminescence cell viability assays. Based on the bioluminescence signal of the firefly luciferin from living U87-Luc cells, which is related to the level of cellular ATP, the cytotoxic assay shows that the nanoconjugate 1-Al—$TiO_2$ has essentially no cytotoxic effect on the glioblastoma cells after 24 h of treatment (FIG. 6) and, therefore, could be considered biocompatible. On the other hand, the cytotoxic effect becomes more apparent as the cells were exposed to the corrole-$TiO_2$ nanoparticles for extended periods of time at higher concentrations (>200 µg/mL). For example, only ca. 65% and ca. 30% of the bioluminescence signals from the live cells were observed after the 48-h and 72-h treatments at 2 mg/mL, respectively. This viability study of the U87-Luc cells treated with 1-Al—$TiO_2$ is also consistent with a study performed on mouse fibroblast cells, using the MTT assay, showing that the cytotoxic effects of $TiO_2$ at various concentrations (3 to 600 µg/mL) were negligible after 24 h of treatment whereas the 48-h treatment of these cells with the nanoparticle showed decrease in cell viability at higher concentrations. Another study on the cytotoxicity effect of unmodified 1-D and 3-D $TiO_2$ on HeLa cell also show that these nanoparticles were relatively nontoxic at concentrations up to 125 µg/mL in the absence of light.

Figure 7:
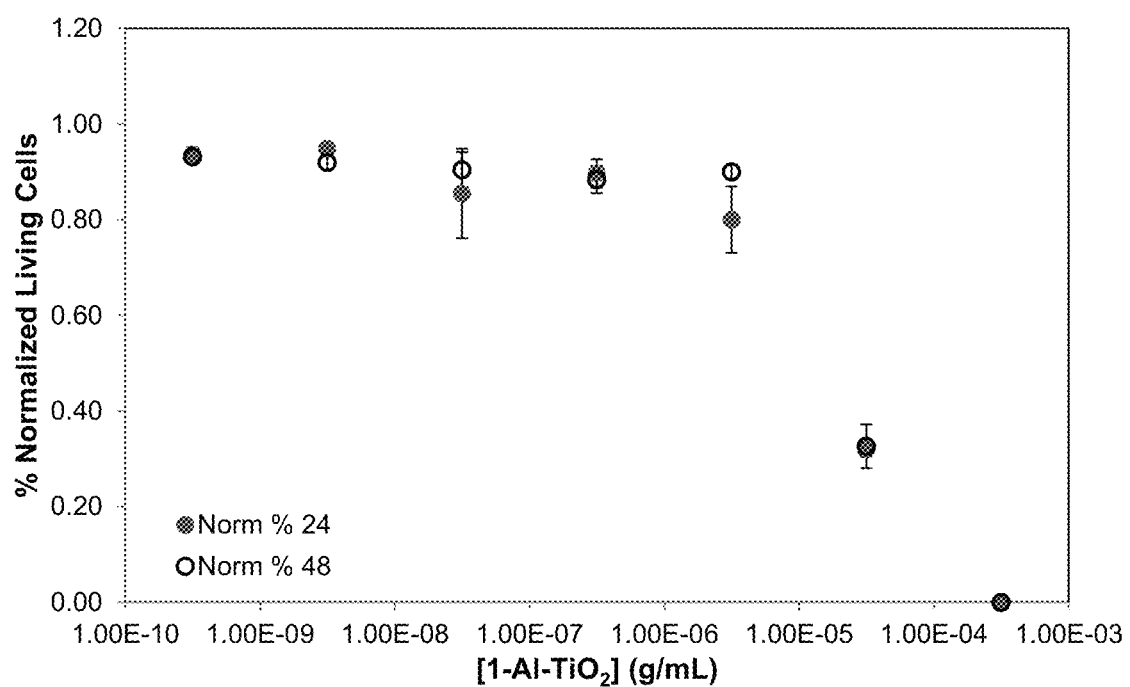
FIG. 7 depicts the results of mouse primary hepatocytes (MPH) treated with a preferred embodiment of the invention (1-Al—$TiO_2$) in various concentrations (0.3 ng/mL to 0.3 mg/mL) for 24 and 48 h.

Additionally, to compare the cytotoxic effect of the nanoconjugate 1-Al—$TiO_2$ on cancer and normal cells, mouse primary hepatocytes (MPH) were treated with 1-Al—$TiO_2$ in various concentrations (0.3 ng/mL to 0.3 mg/mL) for 24 and 48 h (FIG. 7). It was observed that 1-Al—$TiO_2$ was also essentially nontoxic up to 3 mg/mL after both 24 and 48 h of treatment. Only at higher concentrations were the ratios of the live cells dropped below 80%. The MPH behave similarly after 24-h and 48-h treatments with various doses of 1-Al—$TiO_2$, suggesting that low 1-Al—$TiO_2$ concentrations have minimal cytotoxic effects on the viability of these normal cells. While the trend at high concentrations were not observed for the glioblastoma U870-Luc cells treated with 1-Al—$TiO_2$, it is expected that normal cells, especially primary cells, are less tolerant towards exogenous non-native agents. Nonetheless, the intense fluorescence exhibited by 1-Al would allow for the use of the nanoconjugate 1-Al—$TiO_2$ as an optical imaging agent observable by confocal fluorescence microscopy even at low concentrations (20-200 ng/mL) below the cytotoxic thresholds for both the cancer and normal cells observed in the studies.

4-(chlorosulfonyl)Benzoic Acid+$TiO_2$ (Anatase)

Added $TiO_2$ (0.1099 g) and 4-(chlorosulfonyl)Benzoic Acid (0.0171 g) to scintillation vial. Pumped into dry box. Added anhydrous Pyridine (3 mL) and heated to 120° C. for 1 hr, under an inert atmosphere. Allowed to cool to room temperature, then added 2 mL $H_2O$, which then centrifuged down. Washed and centrifuged with acetone, acetone, water, and acetone. Pumped down on high vacuum line to afford product for Infrared Spectroscopy.

Biphenyl-4-sulfonyl Chloride+$TiO_2$ (Anatase)

Added $TiO_2$ (0.1253 g) and Biphenyl-4-sulfonyl Chloride (0.0208 g) to scintillation vial. Pumped into dry box. Added anhydrous Pyridine (3 mL) and heated to 120° C. for 1 hr, under an inert atmosphere. Allowed to cool to room temperature, then added 2 mL $H_2O$, which then centrifuged down. Washed and centrifuged with acetone, acetone, water, and acetone. Pumped down on high vacuum line to afford product for Infrared Spectroscopy.

4'-chlorobiphenyl-4-sulfonyl Chloride+$TiO_2$ (Anatase)

Added $TiO_2$ (0.1205 g) and 4'-chlorobiphenyl-4-sulfonyl Chloride (0.0210 g) to scintillation vial. Pumped into dry box. Added anhydrous Pyridine (3 mL) and heated to 120° C. for 1 hr, under an inert atmosphere. Allowed to cool to room temperature, then added 2 mL $H_2O$, which then centrifuged down. Washed and centrifuged with acetone, acetone, water, and acetone. Pumped down on high vacuum line to afford product for Infrared Spectroscopy.

Chlorsulfonyl Isocyante +$TiO_2$ (Anatase)

Added $TiO_2$ (0.1205 g) to scintillation vial. Pumped into dry box. Added 100 µL Chlorsulfonyl Isocyante. Added anhydrous Pyridine (3 mL) and heated to 120° C. for 1 hr, under an inert atmosphere. Allowed to cool to room temperature, then added 2 mL $H_2O$, which then centrifuged down. Washed and centrifuged with acetone, acetone, water, and acetone. Pumped down on high vacuum line to afford product for Infrared Spectroscopy.

Chlorsulfonyl Isocyante +$TiO_2$ (Anatase)

Added $TiO_2$ (0.1269 g) to scintillation vial. Pumped into dry box. Added 400 µL Chlorsulfonyl Isocyante. Heated to 120° C. for 1 hr, under an inert atmosphere. Allowed to cool to room temperature, then added 4 mL $H_2O$, which was then centrifuged down. Washed and centrifuged with acetone, acetone, water, and acetone. Pumped down on high vacuum line to afford product for Infrared Spectroscopy.

According to the methods described herein, other Cl—$SO_2$-containing substrates can also be employed, such as, for example, 2-pentyl sulfonyl chloride, 3,3,3-trifluoro-propane-1-sulfonyl chloride, methyl(chlorosulfonyl)acetate, and the like.

What is claimed:
1. A material according to formula II

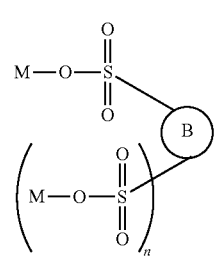

wherein B is

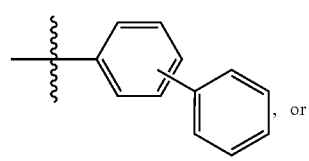

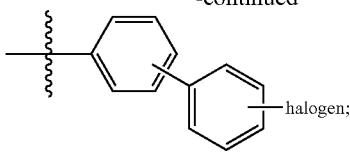

M is a surface comprising $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SiO_2$, $BaTiO_3$, or $ZnO$; and n is 0 or 1.

2. The material according to claim 1, wherein the surface is a nanoparticle surface.

3. The material according to claim 1, wherein n is 0.

4. The material according to claim 1, wherein n is 1.

5. A method of making a material according to claim 1 comprising contacting a surface comprising $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SiO_2$, or $ZnO$, the surface having at least one —OH group;

with a compound of formula IV:

$$Cl-SO_2-R \quad (IV)$$

wherein R is

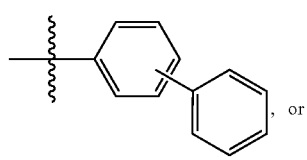

, or

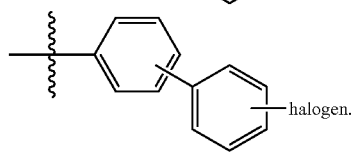

6. The method of claim 5, wherein the surface is a nanoparticle surface.

7. The method according claim 5, wherein n is 0.

8. The method according to claim 5, wherein n is 1.

* * * * *